(12) United States Patent
Nakamura et al.

(10) Patent No.: US 6,797,449 B2
(45) Date of Patent: Sep. 28, 2004

US006797449B2

(54) NEGATIVE IMAGE-RECORDING MATERIAL AND CYANINE DYE

(75) Inventors: Ippei Nakamura, Shizuoka-ken (JP); Tadahiro Sorori, Shizuoka-ken (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 262 days.

(21) Appl. No.: 10/044,959

(22) Filed: Jan. 15, 2002

(65) Prior Publication Data

US 2003/0022094 A1 Jan. 30, 2003

(30) Foreign Application Priority Data

Jan. 15, 2001 (JP) ........................................ 2001-006326
Aug. 6, 2001 (JP) ........................................ 2001-237840

(51) Int. Cl.[7] .......................... G03F 7/021; G03F 7/11; G03F 7/30
(52) U.S. Cl. .................... 430/160; 430/162; 430/271.1; 430/273.1; 430/281.1; 430/920; 430/921; 101/465; 101/466; 101/467
(58) Field of Search ................................. 430/160, 162, 430/271.1, 273.1, 281.1, 920, 921; 101/465, 466, 467

(56) References Cited

U.S. PATENT DOCUMENTS

| | | | |
|---|---|---|---|
| 4,708,925 A | 11/1987 | Newman | |
| 5,037,733 A | 8/1991 | Goda | |
| 5,948,600 A | 9/1999 | Roschger et al. | |
| 6,136,612 A | 10/2000 | Della Ciana et al. | |
| 6,309,792 B1 * | 10/2001 | Hauck et al. | 430/270.1 |
| 6,566,035 B1 * | 5/2003 | Aoshima | 430/270.1 |
| 6,670,098 B1 * | 12/2003 | Kunita | 430/273.1 |
| 2001/0007736 A1 | 7/2001 | Takasaki et al. | |

FOREIGN PATENT DOCUMENTS

| | | |
|---|---|---|
| EP | 0 438 123 A2 | 7/1991 |
| EP | 0 545 380 A1 | 6/1993 |
| EP | 0 694 586 A1 | 1/1996 |
| EP | 0 938 085 A1 | 8/1999 |
| EP | 1 063 231 A1 | 12/2000 |
| EP | 1 096 315 A1 | 5/2001 |
| JP | 07-103171 B2 | 4/1995 |
| WO | WO 01/07524 A1 | 2/2001 |

OTHER PUBLICATIONS

Strekowski, L., et al., *Functionalization of Near–Infrared Cyanine Dyes*, J. Heterocyclic Chem., vol. 33, 1996, pp. 1685–1688.

Gorecki, T., et al., *Synthesis of Novel Near–Infrared Cyanine Dyes for Metal Ion Determination*, J. Heterocyclic Chem., vol. 33, 1996, pp. 1871–1876.

Slominskii et al., "Polymethine Dyes with Hydrocarbon Bridges," Journal of Organic Chemistry of the USSR (Zhumal Organicheskol Khimii), 1978, pp 2046–2051, vol. 14, No. 10, Consultants Bureau, NY, USA (XP–002151108).

Kiprianov et al., "Cyanine Dyes Containing Fluorine," Zh. Obshch. Khim. (English edition), 1950, pp 2187–2193, vol. 20. (XP009001767).

Beilenson et al., "5–Chloro– and 5–Bromo–1–methylbenzthiazole and Cyanine Dyes Prepared From Them," Journal of the Chemical Society, 1936, pp 1225–1231 (XP–009001769).

Brooker et al., "Color and Constitution. VII. Interpretation of Absorptions of Dyes Containing Heterocyclic Nuclei of Different Basicities," Journal of the American Chemical Society, 1945, pp 1875–1889 (XP–002222662).

Brooker et al., "Color and Constitution. V. The Absorption of Unsymmetrical Cyanines. Resonance as a Basis for a Classification of Dyes," Journal of the American Chemical Society, 1942, pp 199–210 (XP–002222663).

* cited by examiner

*Primary Examiner*—John S. Chu
(74) *Attorney, Agent, or Firm*—Burns, Doane, Swecker & Mathis, L.L.P.

(57) ABSTRACT

The invention provides a negative image-recording material for heat-mode exposure systems, which comprises (A) an IR absorbent including cyanine dye having a substituent that contains an atom having an atomic weight of at least 28 such as halogen atom, or a substituent that contains a non-covalent electron pair such as carbonyl group, (B) a radical generator and (C) a radically-polymerable compound, and which is imagewise exposed to IR rays for image formation thereon.

28 Claims, 2 Drawing Sheets

NEGATIVE IMAGE-RECORDING MATERIAL AND CYANINE DYE

BACKGROUND OF THE INVENTION

1. Field of the Invention

The present invention relates to an image-recording material usable for planographic printing plate precursors, color proofs, photoresists and color filters, and to novel cyanine dyes favorable for it. In particular, the invention relates to a negative image-recording material for heat-mode exposure systems, which is usable for a planographic printing plate precursor on which an IR laser is scanned on the basis of the digital signals from a computer or the like to directly make a planographic printing plate; and relates to novel cyanine dyes of high IR absorbing property.

2. Description of the Related Art

For a system of directly making printing plates from digital data of a computer, heretofore proposed have been <1> electrophotography, <2> exposure of photopolymerizable materials to blue or green-emitting lasers, <3> silver salts lamination on photosensitive resin, and <4> silver diffusion transfer photography.

However, these all have some drawbacks. Specifically, the image-forming process of electrophotography <1> is troublesome, in requiring complicated steps of electric charging, exposure to light and development, and this requires a complicated, large apparatus. Photopolymerizable plates for <2> are highly sensitive to blue and green light, and are difficult to handle in light rooms. In the processes of <3> and <4> using silver salts, development is troublesome, and, in addition, the wastes contain silver.

On the other hand, the recent development of laser technology has been remarkable, and high-power, small solid lasers and semiconductor lasers for emitting IR radiation within a wavelength range of from 760 nm to 1200 nm are easily available. For a light source for directly making a printing plate from digital data of a computer or the like, these lasers are extremely useful. However, many practicable photosensitive recording materials are sensitive to visible light falling within a wavelength range of at most 760 nm, to which, therefore, these IR lasers are not applicable for recording images thereon. Accordingly, recording materials capable of being processed with IR lasers are desired.

An image-recording material capable of being processed with an IR laser is described in U.S. Pat. No. 4,708,925, which includes an onium salt, a phenolic resin and a spectral sensitizer. This is a positive image-recording material, in which the onium salt and the phenolic resin express dissolution resistance to developers, and is not a negative image-recording material as in the present invention. On the other hand, a negative image-recording material is disclosed in U.S. Pat. No. 5,340,699, which includes an IR absorber, an acid generator, a resol resin and a novolak resin. For image formation thereon, however, this material requires heat treatment after exposure to a laser. Therefore, a negative image-recording material not requiring heat treatment after exposure to light has been desired.

For example, Japanese Patent Application Publication (JP-B) No. 7-103171 discloses a recording material that includes a cyanine dye having a specific structure, an iodonium salt, and an ethylenically unsaturated double bond-having addition-polymerizable compound. This does not require heat treatment after imagewise exposure to light. However, the strength of the image area of this material is low. Therefore, this is unfavorable for planographic printing plates, as the number of prints from a planographic printing plate is small.

SUMMARY OF THE INVENTION

The object of the invention is to provide a negative image-recording material which can be imagewise exposed to IR rays from an IR-emitting solid laser or semiconductor laser to directly make a printing plate from the digital data of a computer or the like, and which, when the obtained printing plate is used as a planographic printing plate, ensures well cured image formation on the printing plates even though not heated for image formation thereon, and therefore exhibits good printing durability to ensure a large number of good prints from the printing plates; and to provide novel cyanine dyes favorable for IR absorbents for the image-recording material of the type having the excellent characteristics as above.

Having specifically noted the constituent components of negative image-recording materials and having assiduously studied them, the present inventors have found that, when a cyanine dye having a specific partial structure is used for the IR absorbent in a negative image-recording material, then the above-mentioned object can be attained. On the basis of this finding, the present inventors have completed the invention.

Specifically, the invention provides a negative image-recording material for heat-mode exposure systems, which comprises (A) an IR absorbent including cyanine dye having an electron-withdrawing group or a heavy atom-containing substituent in at least one terminal aromatic ring, (B) a radical generator such as onium salts and (C) a radically-polymerizable compound, wherein images are formed therein by imagewise exposure to IR rays.

The invention also provides a negative image-recording material for heat-mode exposure systems, which comprises (A') an IR absorbent of the following general formula (1), (B) a radical generator and (C) a radically-polymerizable compound.

$$A^{+}-Q=B\ X^{-} \qquad (1)$$

wherein

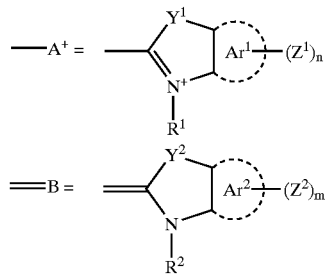

In formula (1), $A^+$ and B are terminal groups represented by the formulae mentioned above; and $R^1$ and $R^2$ each independently represent an optionally-substituted hydrocarbon group having at most 20 carbon atoms. $Ar^1$ and $Ar^2$ may be the same or different, each representing an optionally-substituted aromatic hydrocarbon group or heterocyclic group. $Y^1$ and $Y^2$ may be the same or different, each representing a sulfur atom, an oxygen atom, a selenium atom, a dialkylmethylene group having at most 12 carbon atoms, or —CH=CH—. $Z^1$ and $Z^2$ may be the same or different, each representing a substituent selected from a hydrocarbon group, an oxy group, an electron-withdrawing substituent and a heavy atom-containing substituent, and at least one of $Z^1$ and $Z^2$ is an electron-withdrawing group or a heavy atom-containing substituent. n and m each independently indicate 0 or a positive integer, and the sum of n and m is at least 1.

Q represents a pentamethine group or a heptamethine group, optionally substituted by substituent(s) selected from an alkoxy group, an aryloxy group, an alkylthio group, an arylthio group, a dialkylamino group, a diarylamino group, a halogen atom, an alkyl group, an aralkyl group, a cycloalkyl group, an aryl group, an oxy group and a substituent of the following general formula (2); and Q may have a cyclohexene, cyclopentene or cyclobutene ring containing continuous three methine chains.

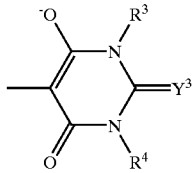

(2)

wherein $R^3$ and $R^4$ each independently represent a hydrogen atom, an alkyl group having from 1 to 8 carbon atoms, or an aryl group having from 6 to 10 carbon atoms; and $Y^3$ represents an oxygen atom or a sulfur atom. $X^-$ represents a counter anion optionally existing for charge neutralization of the compound of formula (1).

Preferably, the cyanine dyes of formula (1) have halogen atoms or carbonyl substituents in the two terminal aromatic rings.

In addition, the present invention provides a negative image-recording material for heat-mode exposure systems, which comprises (A") an IR absorbent of the following general formula (3), (B) a radical generator and (C) a radically-polymerizable compound, wherein images are formed therein by imagewise exposure to IR rays:

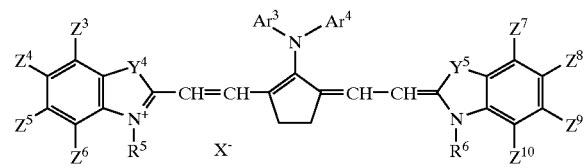

(3)

wherein $R^5$ and $R^6$ each independently represent a linear or branched alkyl group having at most 20 carbon atoms, optionally substituted with any of an aryl group, an alkenyl group, an alkoxy group, a hydroxyl group, a sulfo group, a carboxyl group and an acyloxy group;

$Ar^3$ and $Ar^4$ each independently represent a hydrogen atom, an alkyl group having from 1 to 4 carbon atoms, or an aryl group having from 6 to 10 carbon atoms, the alkyl group and the aryl group for these may be optionally substituted with any of an alkyl group, an aryl group and a halogen atom, and $Ar^3$ and $Ar^4$ may be bonded to each other;

$Y^4$ and $Y^5$ maybe the same or different, each representing a sulfur atom, an oxygen atom, a selenium atom, a dialkylmethylene group having at most 12 carbon atoms, or —CH═CH—;

$Z^3$ to $Z^{10}$ may be the same or different, each representing a hydrogen atom, a hydrocarbon group, an oxy group, an electron-withdrawing group or a heavy atom-containing substituent, and at least one of these is an electron-withdrawing group or a heavy atom-containing substituent, and two neighboring groups of $Z^3$ to $Z^{10}$ may be bonded to each other to form a 5- or 6-membered ring;

$X^-$ represents a counter anion optionally existing for charge neutralization of the compound of formula (1).

Though not clear, the advantages of the negative image-recording material of the invention may result from the action of the cyanine dye therein, which has an electron-withdrawing substituent in at least one terminal aromatic ring in the molecule and which serves as an IR absorbent in the material. Specifically, in the material, the cyanine dye will promote the polymerization of the radically-polymerizable compound to form a firm recording layer, thereby improving the printing durability of the processed material. Concretely, in addition to the decomposition of the ordinary initiator through photo-thermal conversion in the material, the ionization potential of the electron-withdrawing group-substituted cyanine dye therein may be increased, and the cyanine dye excited through exposure to IR rays will readily interact with the initiator to thereby increase the probability of radical generation, and, as a result, the polymerization of the radically-polymerizable compound may be there by promoted. The IR absorbent, cyanine dye having a heavy atom-containing substituent in at least one terminal aromatic ring may also promote the polymerization of the radically-polymerizable compound to thereby enhance the printing durability of the processed material. For this, it is presumed that the IR absorbent will easily undergo triplet excitation when exposed to IR rays, and the thus triplet-excited IR absorbent may inactivate dissolved oxygen acting as a polymerization inhibitor and may promote the decomposition of the radical generator through some interaction with it.

We, the present inventors have further found that novel cyanine compounds having a specific structure are especially useful for the IR absorbent in the recording material of the invention.

Accordingly, the invention also provides a cyanine dye of the following general formula (3-1):

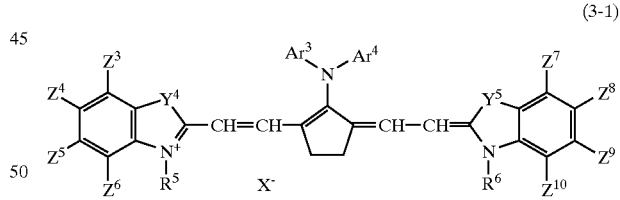

(3-1)

wherein $R^5$ and $R^6$ each independently represent a linear or branched alkyl group having at most 20 carbon atoms, optionally substituted with any of an aryl group, an alkenyl group, an alkoxy group, a hydroxyl group, a sulfo group, a carboxyl group and an acyloxy group; $Ar^3$ and $Ar^4$ each independently represent a hydrogen atom, an alkyl group having from 1 to 4 carbon atoms, or an aryl group having from 6 to 10 carbon atoms, the alkyl group and the aryl group for these may be optionally substituted with any of an alkyl group, an aryl group and a halogen atom, and $Ar^3$ and $Ar^4$ may be bonded to each other; $Y^4$ and $Y^5$ may be the same or different, each representing a sulfur atom, an oxygen atom, a selenium atom, a dialkylmethylene group having at most 12 carbon atoms, or —CH═CH—; $Z^3$ to $Z^{10}$ may be the same or different, each representing a hydrogen atom, a hydrocarbon group, an oxy group, an electron-withdrawing group or a heavy atom-containing substituent, and at least one of these is an electron-withdrawing group or a heavy atom-containing substituent; two neighboring groups of $Z^3$ to $Z^{10}$ may be bonded to each other to form a 5- or 6-membered ring; $X^-$ represents an ion of $CF_3SO_3^-$.

The recording material of the present invention is for "heat-mode exposure", and this means that the recording material is subjected to heat-mode exposure for image formation. The specifics of heat-mode exposure are described in detail below. As in Hans-Joachim Timpe, IS & Ts NIP 15:1999 *International Conference on Digital Printing Technologies*, page 209, it is known that, with regard to a process comprising photo-excitation of a light-absorbing substance (e.g., dye) in a photographic material followed by chemical or physical change thereof for image formation in a layer of the material, the process of image formation comprising photo-excitation of the light-absorbing substance followed by chemical or physical change thereof includes two major modes. Specifically, one is a photon mode in which the photo-excited light-absorbing substance in the photographic material is inactivated through photochemical interaction (for example, energy transfer or electron transfer) with another reactive substance in the material, and the reactive substance having been thus activated as a result of the interaction undergoes a chemical or physical change necessary for image formation in the layer of the material; and the other is a heat mode in which the photo-excited light-absorbing substance in the photographic material generates heat and is thus inactivated through the heat generation, and the other reactive substance in the material receives the heat and undergoes a chemical or physical change necessary for image formation in a layer of the material. Other minor modes of the process are omitted herein; for example, ablation, in which the substances in a photographic material are explosively scattered by some locally focused light energy, and multiphoton absorption, in which one molecule in a photographic material absorbs a number of photons all at one time.

The modes of the exposure process are referred to as photon-mode exposure and heat-mode exposure. The technical difference between photon-mode exposure and heat-mode exposure is whether or not energy quantities from a plurality of photons for exposure can be added up for the intended reaction. For example, referred to is a reaction through exposure to a number, n, of photons. In the photon-mode exposure, which takes advantage of photo-chemical interaction of the substances in a photographic material, the energy quantities from the n photons cannot be added up for the reaction because of laws of quantum energy and momentum conservation. In other words, every reaction through photon-mode exposure requires the condition "quantity of energy of one photon≧quantity of energy for one reaction". On the other hand, in the heat-mode exposure, the light-absorbing substance in the photographic material is first photo-excited to generate heat, and the heat thus having been converted from light energy serves for the reaction for image formation in a layer of the material. Accordingly, in the heat-mode exposure, the energy quantities of all n photons can be added up for image formation. Therefore, the condition of "energy quantity of n photons≧energy quantity for one reaction" will be sufficient for the heat-mode exposure. However, the addition of the energy quantities in the heat-mode exposure is restricted by heat diffusion. Specifically, if an exposed area (reaction point) of a photographic material successively undergoes a subsequent photo-excitation and inactivation before heat generated therein by a previous photo-excitation and inactivation step goes out through heat diffusion, and therefore successively receives heat through successive photo-excitations and inactivations, then the heat quantities can be surely accumulated and added up to elevate the temperature of that exposed area. However, if the heat generation in the subsequent step is too late, the heat generated in the previous step will go out of the area through heat diffusion. In other words, in heat-mode exposure to a predetermined level of total energy, a case of short-time exposure to higher energy and a case of long-time exposure to lower energy produce different results, and the former case of short-time exposure to higher energy is more advantageous than the latter case.

Needless-to-say, the photon-mode exposure may also undergo the same phenomenon as above, being influenced by subsequent reaction diffusions, but is basically free from this phenomenon.

The difference between the photon-mode exposure and the heat-mode exposure will be discussed with respect to the characteristics of a photographic material to be processed. In the photon-mode exposure, intrinsic sensitivity (the quantity of energy necessary for the reaction for image formation) of a photographic material is always constant relative to the exposure power density ($W/cm^2$) (=energy density per unit exposure time); but in the heat-mode exposure, the intrinsic sensitivity increases with an increase in the exposure power density. Now, the exposure time is fixed to suffice for practicable image-recording materials, and the two modes are compared for the thus-fixed exposure time. In photon-mode exposure, in general, a low degree of energy of about $0.1~mJ/cm^2$ or so may be enough for high-sensitivity exposure of the materials, but even a slight amount of exposure will cause photo-reaction in the materials. Therefore, in this mode, the materials often involve a problem of low-exposure fogging in a non-exposed area. On the other hand, in heat-mode exposure, the photographic materials do not undergo photo-reaction if the amount of exposure is not above a certain level. In this mode, in general, the photographic materials require a level of exposure energy of 50 $mJ/cm^2$ or so, in view of their thermal stability, and are therefore free from the problem of low-exposure fogging in the non-exposed area.

In fact, in heat-mode exposure, photographic materials require an exposure power density of at least 5000 $W/cm^2$ on their surface, preferably at least 10000 $W/cm^2$. Though not described in detail herein, high-power density lasers of higher than $5.0 \times 10^5~W/cm^2$ are undesirable, as they cause ablation and soil light sources and other units.

DETAILED DESCRIPTION OF THE PREFERRED EMBODIMENTS

Figure 1:
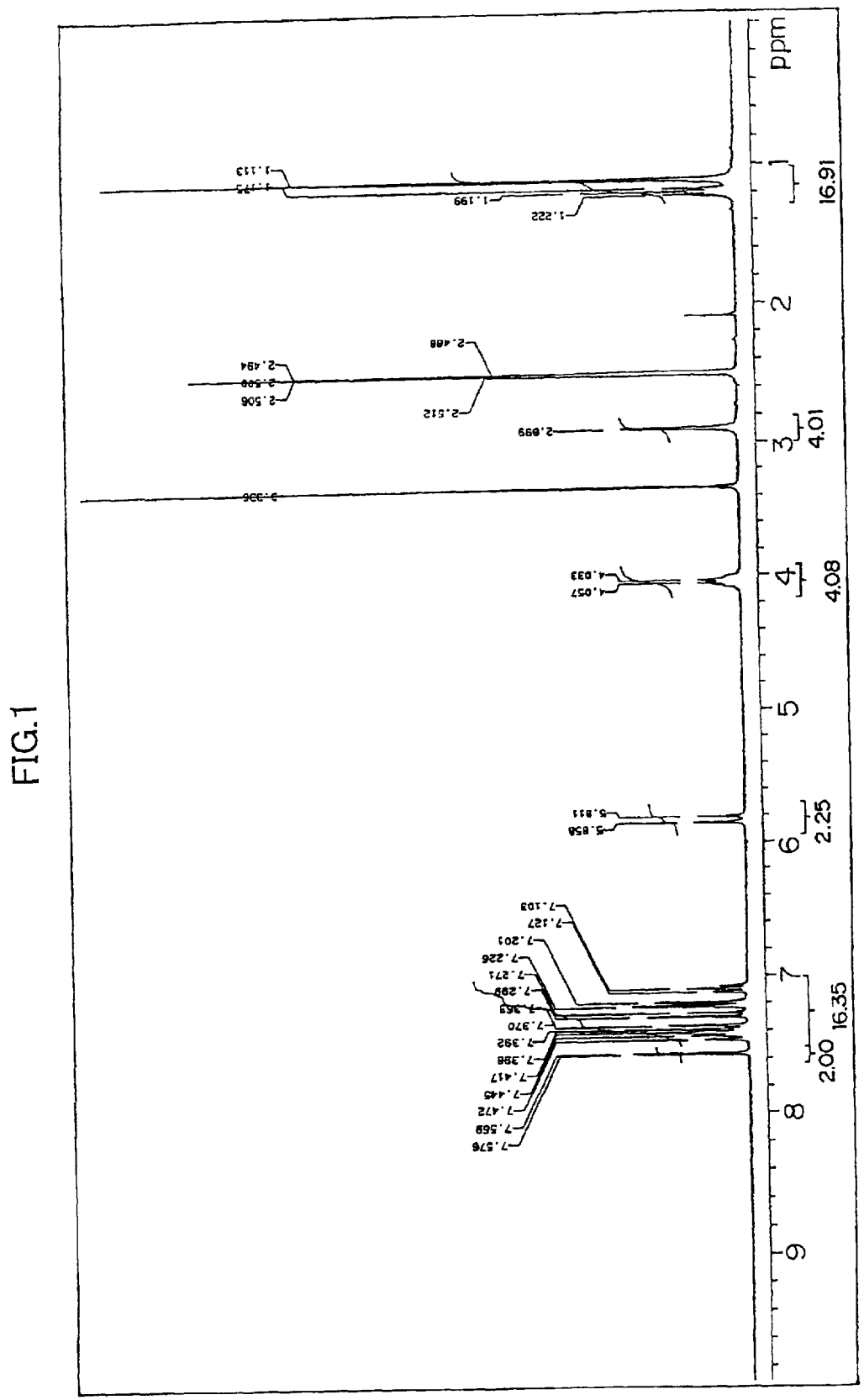
FIG. 1 is the $^1$H-NMR spectrum (DMSO-$d_6$) of an IR absorbent, IR-2.

The invention is described in detail hereinunder. (A) IR absorbent, cyanine dye having an electron-withdrawing group or a heavy atom-containing substituent in at least one terminal aromatic ring:

The IR absorbent to be used in the recording material of the invention is a cyanine dye (A-1) having an electron-withdrawing group in at least one terminal aromatic ring, or a cyanine dye (A-2) having a heavy atom-containing substituent in at least one terminal aromatic ring.

First described is the cyanine dye (A-1) having an electron-withdrawing group in at least one terminal aromatic ring. Preferably, the electron-withdrawing group has a Hammett's substituent constant, $\sigma_{para}$, of at least 0.01, more preferably at least 0.20, even more preferably at least 0.30. Preferred examples of the electron-withdrawing group having $\sigma_{para}$ of at least 0.05 are halogen atoms such as fluorine (0.06), chlorine (0.30), bromine (0.27), iodine (0.30); carbonyl substituents such as —CHO (0.22), —COCH$_3$ (0.50), —COC$_6$H$_5$ (0.46), —CONH$_2$ (0.36), —COO$^-$ (0.30), —COOH (0.41), —COOCH$_3$ (0.39), —COOC$_2$H$_5$ (0.45); sulfonyl or sulfinyl substituents such as —SOCH$_3$ (0.49), —SO$_2$CH$_3$ (0.72), —SO$_2$C$_6$H$_5$, —SO$_2$CF$_3$ (0.93), —SO$_2$NH$_2$ (0.57), —SO$_2$OC$_6$H$_5$, —SO$_3^-$ (0.09), —SO$_3$H (0.50); nitrogen-containing substituents such as —CN (0.01), —N(CH$_3$)$_3^+$ (0.82), —N(CF$_3$)$_2$ (0.53); and halogen-containing substituents such as —CCl$_3$, —CH$_2$Cl (0.18), —CHCl$_2$, —CF$_3$ (0.54). (The parenthesized numerals are the data of $\sigma_{para}$ of the substituents.)

Preferred examples of the substituent having an electron-withdrawing group are those having a non-covalent electron pairs, and they include, for example, carbonyl-having substituents, sulfonyl-having substituents, sulfinyl-having substituents, ether bond-having substituents. Of those, preferred are carbonyl-having substituents. Concretely, they are, for example, an acyl group such as acetyl or benzoyl group; an alkoxycarbonyl or aryloxycarbonyl group such as methoxycarbonyl or toluyloxycarbonyl group; an amido group such as diethylaminocarbonyl group; and a carboxyl group. The carbonyl-having substituent may be bonded to the aromatic group via a divalent or higher polyvalent linking group therebetween.

Next described is the cyanine dye (A-2) having a heavy atom-containing substituent in at least one terminal aromatic ring. In the heavy atom-containing substituent, the heavy atom preferably has an atomic weight of at least 28. The heavy atom-containing substituent is described. Preferred examples of the atom having an atomic weight of at least 28 in the substituent that the cyanine dye of the type has are silicon (28.09), phosphorus (30.97), sulfur (32.07), chlorine (35.45), germanium (72.61), arsenic (74.92), selenium (78.96), bromine (79.90), tin (118.71), antimony (121.76), tellurium (127.60) and iodine (126.90). (The atomic weight is parenthesized). In view of their safety and easy availability, more preferred are silicon, phosphorus, sulfur and halogen atoms such as chlorine, bromine and iodine; and even more preferred are halogen atoms.

Either singly or as combined with any other atoms, the atom having an atomic weight of at least 28 forms a substituent in at least one terminal aromatic ring in the cyanine dye, and the substituent may be bonded to the aromatic ring via a divalent linking group therebetween.

Preferred examples of the silicon-containing substituent are those having an alkyl or aryl group bonded to silicon, such as trimethylsilyl, t-butyldimethylsilyl and dimethylphenylsilyl groups. The phosphorus-containing substituent includes those having an alkyl or aryl group bonded to phosphorus, such as dimethylphoshino and diphenylphosphino groups, as well as a phosphono group. The sulfur-containing substituent includes residues of phosphorus-containing acids and their salts and ester derivatives, for example, an alkyl or arylsulfonyl group such as methylsulfonyl and phenylsulfonyl groups; an alkyl or arylsulfinyl group such as ethylsulfinyl a n d toluylsulfinyl group; sulfo, sulfino and sulfeno group; and an alkyl or arylthio group such as methylthio and phenylthio groups. Halogen atoms may be the substituent by themselves; and the halogen-containing substituent includes a halogen-substituted alkyl group and a halogen-substituted aryl group.

For the chromophoric group which is common to the IR absorbents, preferred are cyanine dyes in view of their image producibility, absorption wavelength latitude, solubility and stability. More preferred are heptamethine-cyanine dyes having any of indolenine, benzoindolenine, benzothiazole, benzoxazole and benzoselenazole skeletons in view of their image producibility and absorption wavelength latitude; and most preferred are those having an indolenine or benzoindolenine skeleton.

Of the dyes having the chromophoric group as above, especially preferred are cyanine dyes of the following general formula (A'):

$$A^+ - Q = B \ X^-  \qquad (1)$$

wherein

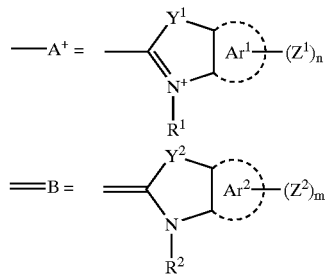

In formula (1), A$^+$ and B are terminal groups represented by the formulae mentioned above; and R$^1$ and R$^2$ each independently represent an optionally-substituted hydrocarbon group having at most 20 carbon atoms, preferably an alkyl group having from 1 to 4 carbon atoms. Ar$^1$ and Ar$^2$ may be the same or different, each representing an optionally-substituted aromatic hydrocarbon group or heterocyclic group. For the aromatic hydrocarbon group, preferred are benzene and naphthalene rings; and for the heterocyclic group, preferred are pyridine and pyrazine rings. Especially preferred are benzene and naphthalene rings. Y$^1$ and Y$^2$ may be the same or different, each representing a sulfur atom, an oxygen atom, a selenium atom, a dialkylmethylene group having at most 12 carbon atoms, or —CH=CH—, preferably a dialkylmethylene group such as dimethylmethylene. Z$^1$ and Z$^2$ may be the same or different, each representing a substituent selected from a hydrocarbon group, an oxy group, an electron-withdrawing substituent and a heavy atom-containing substituent, and at least one of these is an electron-withdrawing group or a heavy atom-containing substituent. For the electron-withdrawing substituent and the heavy atom-containing substituent, preferred area halogen atom, an optionally-substituted carbonyl group, an optionally-substituted sulfonyl group, a thio group, an alkyl halide group, and a silyl group; and more preferred are a halogen atom, an alkoxycarbonyl group, and an alkyl halide group. n and m each independently indicate 0 or a positive integer, and the sum of n and m is at least 1.

Q represents a pentamethine group or a heptamethine group, but preferably a heptamethine group in view of the IR exposure latitude and the stability of the compounds. Q may be optionally substituted by substituent(s) selected from an alkoxy group, an aryloxy group, an alkylthio group, an arylthio group, a dialkylamino group, a diarylamino group, a halogen atom, an alkyl group, an aralkyl group, a cycloalkyl group, an aryl group, an oxy group, an iminium base, and a substituent of the following general formula (2). Preferred substituents for Q are a diarylamino group such as diphenylamino, and an arylthio group such as phenylthio. Preferably, Q has a cyclohexene, cyclopentene or cyclobutene ring containing continuous three methine chains, more preferably such a cyclopentene or cyclohexene ring.

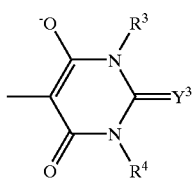

(2)

wherein $R^3$ and $R^4$ each independently represent a hydrogen atom, an alkyl group having from 1 to 8 carbon atoms, or an aryl group having from 6 to 10 carbon atoms; and $Y^3$ represents an oxygen atom or a sulfur atom. $X^-$ represents a counter anion optionally existing for charge neutralization of the compound of formula (1). From the viewpoint of the storage stability of the coating liquid for the recording layer of the material, $X^-$ is preferably a halide ion, a perchlorate ion, a tetrafluoroborate ion, a hexafluorophosphate ion or a sulfonate ion, more preferably a perchlorate ion or a sulfonate ion.

Of the dyes having the chromophoric group as above, especially preferred are those of the following general formula (3):

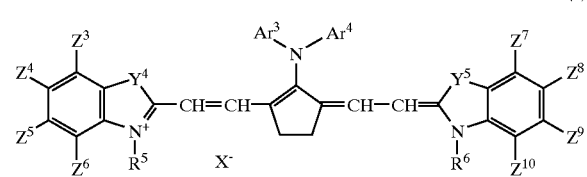

(3)

In formula (3), $R^5$ and $R^6$ each independently represent an optionally-substituted hydrocarbon group having at most 20 carbon atoms, preferably an alkyl group having from 1 to 4 carbon atoms. $Ar^3$ and $Ar^4$ maybe the same or different, each representing a hydrogen atom, an alkyl group having from 1 to 4 carbon atoms, or an aryl group having from 6 to 10 carbon atoms, but preferably a phenyl group. $Y^4$ and $Y^5$ may be the same or different, each representing a sulfur atom, an oxygen atom, a selenium atom, a dialkylmethylene group having at most 12 carbon atoms, or —CH=CH—, but preferably a dialkylmethylene group such as dimethylmethylene. $Z^3$ to $Z^{10}$ may be the same or different, each representing a hydrogen atom, an electron-withdrawing group, or a heavy atom-containing substituent, and at least one of these is an electron-withdrawing substituent or a heavy atom-containing substituent of those mentioned hereinabove, and particularly preferred are a halogen atom and an alkoxycarbonyl group. $X^-$ has the same meaning as in formula (1).

Of the dyes of formula (3), those in which $X^-$ is an ion of $CF_3SO_3^-$, or that is, the cyanine dyes of the above-mentioned formula (3-1) are novel compounds, and are especially favorable for the IR absorbent for use in the invention.

Specific examples of the IR absorbent favorable for use in the invention are given in the following Tables 1 to 8 showing the skeleton of the chromophoric group and the substituents of the exemplified compounds, to which, however, the invention is not whatsoever limited. Of the IR absorbents (cyanine dyes) given in Tables 1 to 8, IR-2, IR-6, IR-8, IR-11 and IR-33 are novel compounds of formula (3-1) in which $X^-$ is an ion of $CF_3SO_3^-$.

TABLE 1

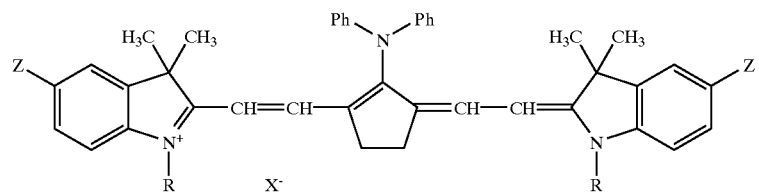

|  | Z | R | $X^-$ |
| --- | --- | --- | --- |
| IR-1 | Cl | $C_2H_5$ | $ClO_4^-$ |
| IR-2 | Cl | $C_2H_5$ | $CF_3SO_3^-$ |
| IR-3 | Br | $C_3H_7$ | $ClO_4^-$ |
| IR-4 | Br | $C_6H_{13}$ | $PF_6^-$ |
| IR-5 | I | $C_2H_5$ | $ClO_4^-$ |
| IR-6 | I | $C_4H_9$ | $CF_3SO_3^-$ |
| IR-7 | $CO_2C_2H_5$ | $C_2H_5$ | $ClO_4^-$ |
| IR-8 | $SCF_3$ | $CH_3$ | $CF_3SO_3^-$ |
| IR-9 | $SO_2CF_3$ | $CH_3$ | $ClO_4^-$ |
| IR-10 | Cl | $CH_3$ | $BF_4^-$ |
| IR-11 | $CF_3$ | $C_2H_5$ | $CF_3SO_3^-$ |

TABLE 2

| | Z | R | Y | n | X⁻ |
|---|---|---|---|---|---|
| IR-12 | Cl | $C_2H_5$ | Cl | 2 | $ClO_4^-$ |
| IR-13 | $CO_2CH_3$ | $CH_3$ | Cl | 2 | $BF_4^-$ |
| IR-14 | Br | $C_2H_5$ | SPh | 3 | $CF_3SO_3^-$ |
| IR-15 | Cl | $C_2H_5$ | OPh | 3 | $ClO_4^-$ |
| IR-16 | I | $CH_3$ | Cl | 3 | $I^-$ |
| IR-17 | $SO_2CF_3$ | $C_3H_7$ | SPh | 3 | $ClO_4^-$ |
| IR-18 | COPh | $CH_3$ | (thiobarbiturate group) | 3 | — |

TABLE 3

| | Z | R | X⁻ |
|---|---|---|---|
| IR-19 | $SCF_3$ | $CH_3$ | $ClO_4^-$ |
| IR-20 | $SO_2CF_3$ | $C_2H_5$ | $H_3C\text{-}C_6H_4\text{-}SO_3^-$ |
| IR-21 | $SCH_3$ | $CH_3$ | $BF_4^-$ |

TABLE 4

| | Z | R | X⁻ |
|---|---|---|---|
| IR-22 | $CO_2CH_3$ | $CH_3$ | $ClO_4^-$ |
| IR-23 | $SO_2OC_2H_5$ | $CH_2C_6H_5$ | $CF_3SO_3^-$ |

TABLE 5

| | Z | R | X⁻ |
|---|---|---|---|
| IR-24 | CO$_2$CH$_3$ | CH$_3$ | ClO$_4^-$ |
| IR-25 | CO$_2$Ph | CH$_2$CH(CH$_2$)$_3$CH$_3$<br>\|<br>CH$_2$CH$_3$ | BF$_4^-$ |

TABLE 6

| | Z | R | X⁻ |
|---|---|---|---|
| IR-26 | Br | C$_2$H$_5$ | ClO$_4^-$ |
| IR-27 | SO$_2$OC$_2$H$_5$ | CH$_3$ | CF$_3$SO$_3^-$ |

TABLE 7

| | Z | R | Y$^1$ | Y$^2$ | X⁻ |
|---|---|---|---|---|---|
| IR-28 | Cl | CH$_3$ | Cl | S | ClO$_4^-$ |
| IR-29 | Br | CH$_2$(CH$_2$)$_8$CH$_3$ | SPh | S | Br⁻ |
| IR-30 | COCH$_3$ | CH$_2$CH=CH$_2$ | Cl | O | SbF$_6^-$ |
| IR-31 | CO$_2$C$_2$H$_5$ | CH$_3$ | NPh$_2$ | S | BF$_4^-$ |

TABLE 8

| | Z$^1$ | Z$^2$ | R$^1$ | R$^2$ | X⁻ |
|---|---|---|---|---|---|
| IR-32 | Cl | H | C$_2$H$_5$ | C$_2$H$_5$ | ClO$_4^-$ |
| IR-33 | Cl | CH$_3$ | C$_2$H$_5$ | CH$_3$ | CF$_3$SO$_3^-$ |
| IR-34 | Cl | C(CH$_3$)$_3$ | CH$_3$ | CH$_3$ | ClO$_4^-$ |
| IR-35 | I | Cl | C$_2$H$_5$ | C$_2$H$_5$ | ClO$_4^-$ |

One or more of the above-mentioned IR absorbents may be used herein either singly or as combined.

Not interfering with the effect of the invention, any ordinary IR absorbents apart from the specific IR absorbents of formulae (A-1), (A-2) and (A') may be added to the recording material of the invention. In that case, the amount of the additional ordinary IR absorbent to be in the recording material is preferably at most 40% by weight of the total solid content of all the IR absorbents therein.

The IR absorbents that may be additionally in the recording material of the invention are not specifically defined in point of their absorption wavelength range, and may be any and every one having the function of converting the light which it has absorbed into heat for image formation in the recording material. For these, however, preferred are IR-absorbing dyes and pigments that have an absorption peak in a wavelength range falling between 760 nm and 1200 nm, as being well applicable to easily-available high-power lasers.

A dye may be any of commercially-available dyes and any of other known dyes, for example, those described in *Dye Handbook* (the Association of Organic Synthetic Chemistry, 1970). Specifically, examples include azo dyes, metal-complex azo dyes, pyrazolonazo dyes, naphthoquinone dyes, anthraquinone dyes, phthalocyanine dyes, carbonium dyes, quinonimine dyes, methine dyes, cyanine dyes, squarylium dyes, pyrylium salts, metal thiolate complexes, oxonol dyes, diimmonium dyes, aminium dyes, croconium dyes and the like.

Preferred dyes for use herein include cyanine dyes such as those described in Japanese Patent Application Laid-Open (JP-A) Nos. 58-125246, 59-84356, 59-202829 and 60-78787; methine dyes as in JP-A Nos. 58-173696, 58-181690 and 58-194595; naphthoquinone dyes as in JP-A Nos. 58-112793, 58-224793, 59-48187, 59-73996, 60-52940 and 60-63744; squarylium dyes as in JP-A No. 58-112792; and cyanine dyes as in British Patent No. 434,875.

Also preferred for use herein are near-IR absorbing sensitizers such as those described in U.S. Pat. No. 5,156,938; substituted arylbenzo (thio) pyrylium salts as in U.S. Pat. No. 3,881,924; trimethine-thiapyrylium salts as in JP-A No. 57-142645 (U.S. Pat. No. 4,327,169); pyrylium compounds as in JP-A Nos. 58-181051, 58-220143, 59-41363, 59-84248, 59-84249, 59-146063 and 59-146061; cyanine dyes as in JP-A No. 59-216146; pentamethine-thiopyrylium salts as in U.S. Pat. No. 4,283,475; and pyrylium compounds as in JP-B Nos. 5-13514 and 5-19702.

Other examples preferred for the dyes for use herein are near-IR absorbing dyes of formulae (I) and (II) in U.S. Pat. No. 4,756,993.

Of those dyes, especially preferred are cyanine dyes, phthalocyanine dyes, oxonol dyes, squalilium dyes, pyrylium salts, thiopyrylium dyes, and nickel-thiolate complexes. More preferred are dyes of general formulae (a) to (e) mentioned below, as ensuring good photo-thermal conversion efficiency. Most preferred are the cyanine dyes of formula (a), as ensuring high polymerization activity when used in the polymerizable composition of the invention, and as stable and economical.

General Formula (a)

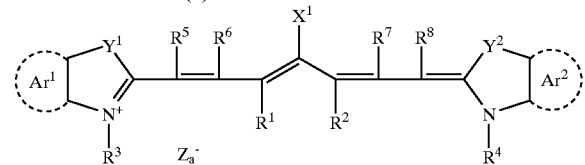

In formula (a), $X^1$ represents a halogen atom, a halogen atom, —$NPh_2$, $X^2$—$L^1$, or a group of

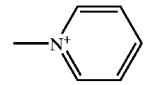

$X^2$ represents an oxygen or sulfur atom; $L^1$ represents a hydrocarbon group having from 1 to 12 carbon atoms, or a hetero atom-containing aromatic group, or a hetero atom-containing hydrocarbon group having from 1 to 12 carbon atoms. The hetero atom includes N, S, O halogen atoms, and Se.

$R^1$ and $R^2$ each independently represent a hydrocarbon group having from 1 to 12 carbon atoms. In view of the storage stability of the coating liquid for the photosensitive layer containing the dye, $R^1$ and $R^2$ each are preferably a hydrocarbon group having at least 2 carbon atoms; more preferably, $R^1$ and $R^2$ are bonded to each other to form a 5-membered or 6-membered ring.

$Ar^1$ and $Ar^2$ may be the same or different, and each represents an optionally-substituted aromatic hydrocarbon group. Preferably, the aromatic hydrocarbon group for them is a benzene ring or a naphthalene ring. Preferred substituents for them are a hydrocarbon group having at most 12 carbon atoms, a halogen atom, and an alkoxy group having at most 12 carbon atoms. $Y^1$ and $Y^2$ may be the same or different, and each represents a sulfur atom, or a dialkylmethylene group having at most 12 carbon atoms. $R^3$ and $R^4$ may be the same or different, and each represents an optionally-substituted hydrocarbon group having at most 20 carbon atoms. Preferred substituents for them are an alkoxy group having at most 12 carbon atoms, a carboxyl group, and a sulfo group. $R^5$, $R^6$, $R^7$ and $R^8$ may be the same or different, and each represents a hydrogen atom, or a hydrocarbon group having at most 12 carbon atoms. Preferably, these are hydrogen atoms, as the starting materials for the dyes are easily available. $Z_a^-$ represents a counter anion. However, in case where any of $R^1$ to $R^8$ is substituted with a sulfo group, $Z_a^-$ is unnecessary. In view of the storage stability of the coating liquid for the photosensitive layer containing the dye, $Z_a^-$ is preferably a halide ion, a perchlorate ion, a tetrafluoroborate ion, a hexafluorophosphate ion, or a sulfonate ion, more preferably a perchlorate ion, a hexafluorophosphate ion or an arylsulfonate ion.

Examples of the cyanine dyes of formula (a) preferred for use in the invention are shown below. In addition to these, also preferred for use herein are the dyes described in paragraphs [0017] to [0019] in Japanese Patent Application No. 11-310623, paragraphs [0012] to [0038] in Japanese Patent Application No. 2000-224031, and paragraphs [0012] to [0023] in Japanese Patent Application No. 2000-211147.

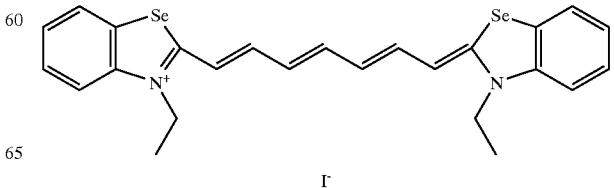

I

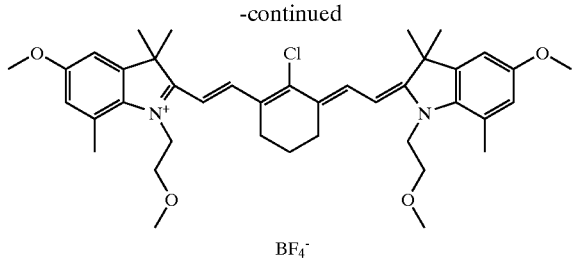
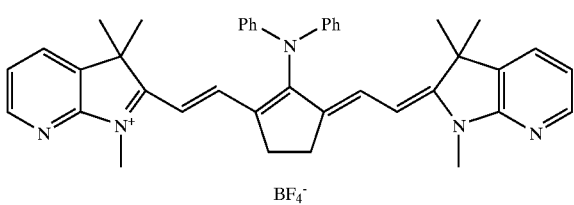
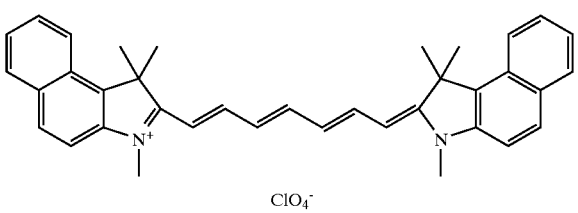
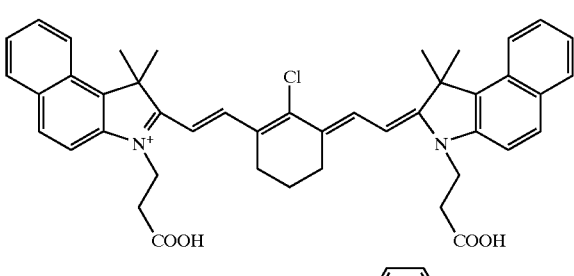
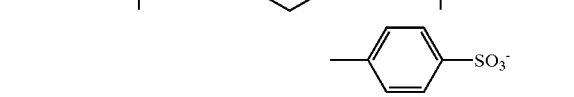
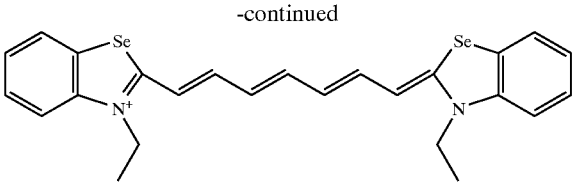
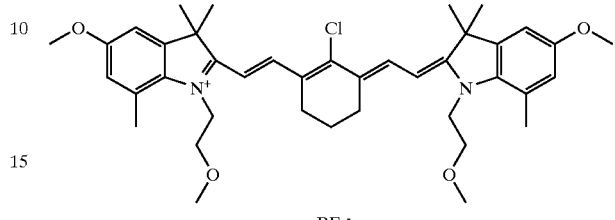
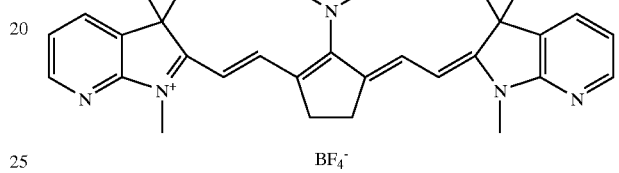
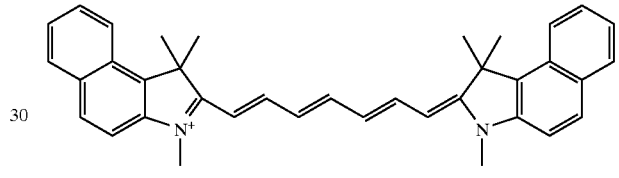
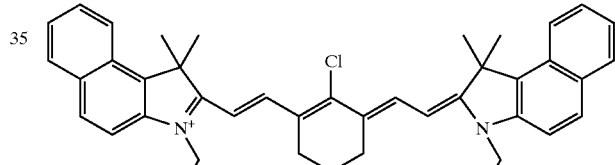
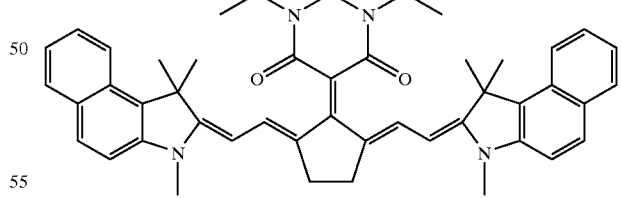
General Formula (b)
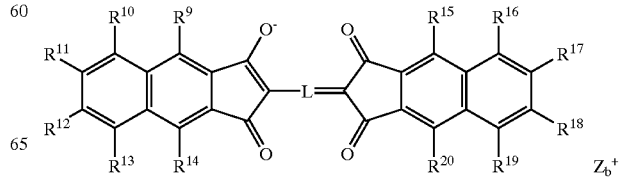

In formula (b), L represents a methine chain having at least 7 conjugated carbon atoms, and the methine chain may be optionally substituted. The substituents, if any, in the methine chain may be bonded to each other to form a cyclic structure. $Z_b^+$ represents a counter cation. Preferred examples of the counter cation are ammonium, iodonium, sulfonium, phosphonium, pyridinium, and alkali metal cations ($Ni^+$, $K^+$, $Li^+$). $R^9$ to $R^{14}$, and $R^{15}$ to $R^{20}$ each independently represent a hydrogen atom, or a substituent selected from a halogen atom, a cyano group, an alkyl group, an aryl group, an alkenyl group, an alkynyl group, a carbonyl group, a thio group, a sulfonyl group, a sulfinyl group, an oxy group and an amino group, or a substituent of two or three of the groups combined; and they may be bonded to each other to form a cyclic structure. Of the dyes of formula (b), preferred are those in which L is a methine chain having 7 conjugated carbon atoms, and $R^9$ to $R^{14}$, and $R^{15}$ to $R^{20}$ are all hydrogen atoms, as easily available and effective.

Examples of the dyes of formula (b) preferred for use in the invention are shown below.

Examples of the dyes of formula (c) preferred for use in the invention are shown below.

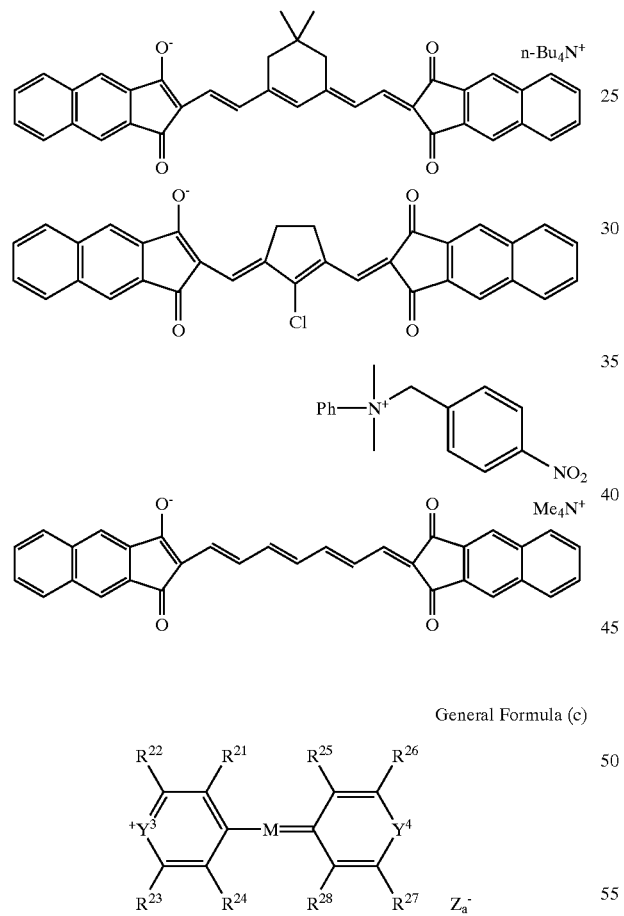

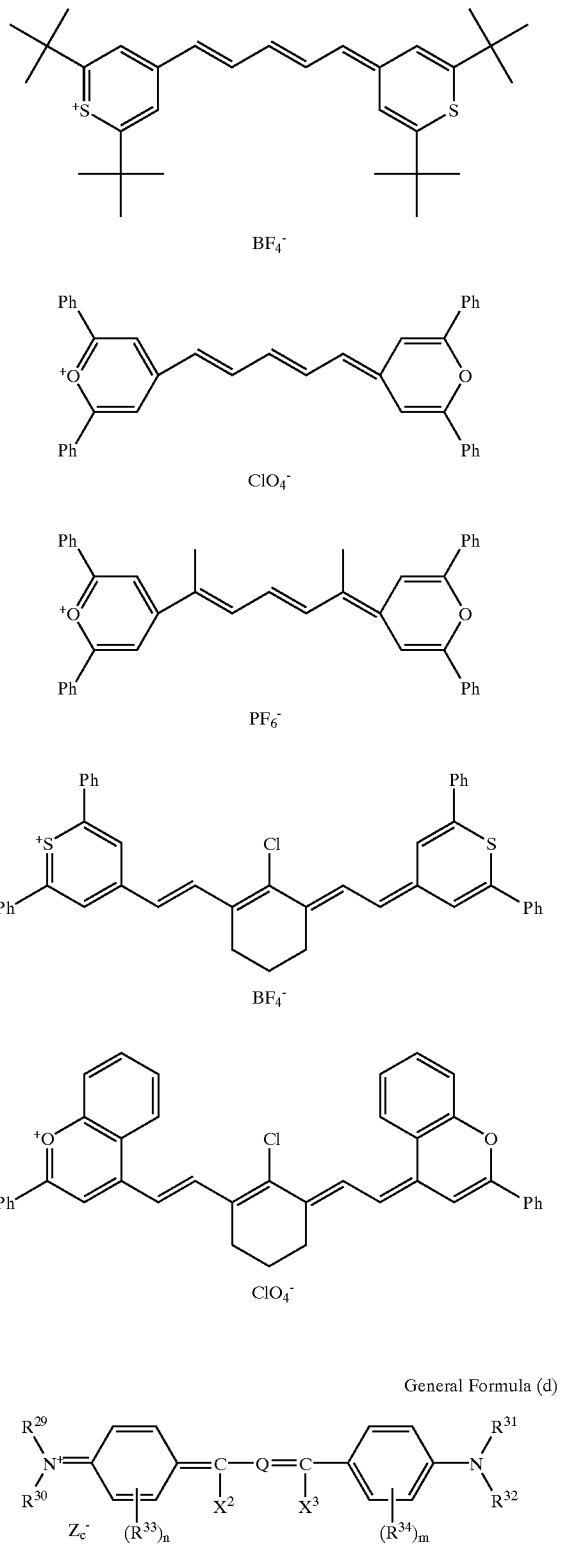

In formula (c), $Y^3$ and $Y^4$ each represent an oxygen atom, a sulfur atom, a selenium atom, or a tellurium atom; M represents a methine chain having at least 5 conjugated carbon atoms; $R^{21}$ to $R^{24}$, and $R^{25}$ to $R^{28}$ may be the same or different, each representing a hydrogen atom, a halogen atom, a cyano group, an alkyl group, an aryl group, an alkenyl group, an alkynyl group, a carbonyl group, a thio group, a sulfonyl group, a sulfinyl group, an oxy group or an amino group; $Z_a^-$ represents a counter anion, having the same meaning as in formula (a).

In formula (d), $R^{29}$ to $R^{32}$ each independently represent a hydrogen atom, an alkyl group or an aryl group; $R^{33}$ and $R^{34}$ each independently represent an alkyl group, a substituted oxy group, or a halogen atom; n and m each independently indicate an integer of from 0 to 4. $R^{29}$ and $R^{30}$, and $R^{31}$ and $R^{32}$ may be bonded to each other to form a ring. $R^{29}$ and/or $R^{30}$ may be bonded to $R^{33}$, and $R^{31}$ and/or $R^{32}$ to $R^{34}$, to form a ring. Plural $R^{33}$'s or $R^{34}$'s, if any, may be bonded to each other to form a ring. $X^2$ and $X^3$ each independently represent a hydrogen atom, an alkyl group or an aryl group; and at lease one of $X^2$ and $X^3$ is a hydrogen atom or an alkyl group. Q represents an optionally-substituted trimethine or pentamethine group, and it may form a cyclic structure along with a divalent organic group. $Z_c^-$ represents a counter anion, having the same meaning as that of $Z_a^-$ in formula (a).

Examples of the dyes of formula (d) preferred for use in the invention are shown below.

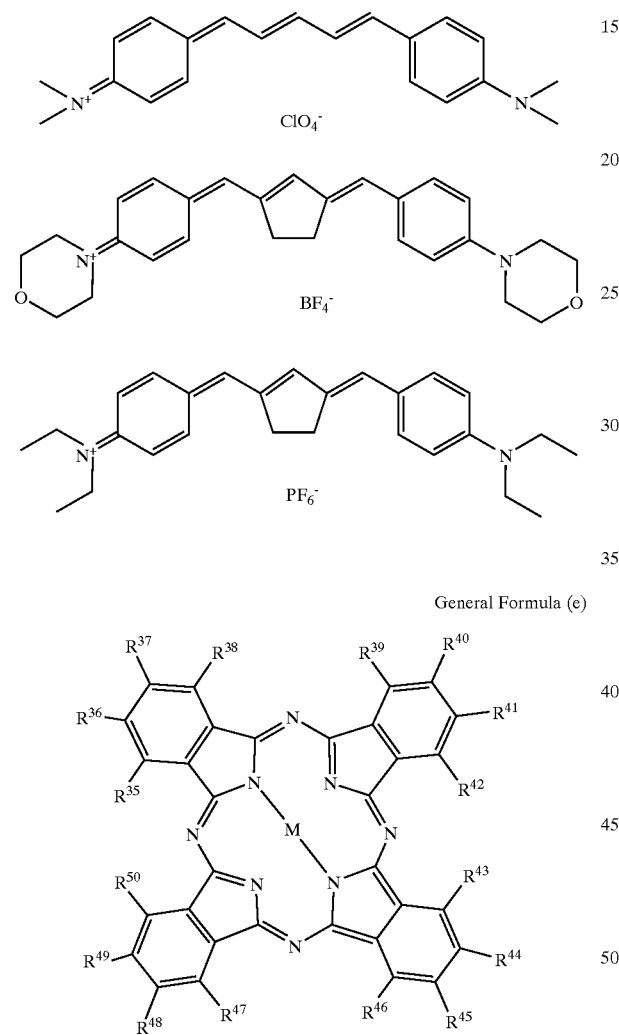

Examples of the dyes of formula (e) preferred for use in the invention are shown below.

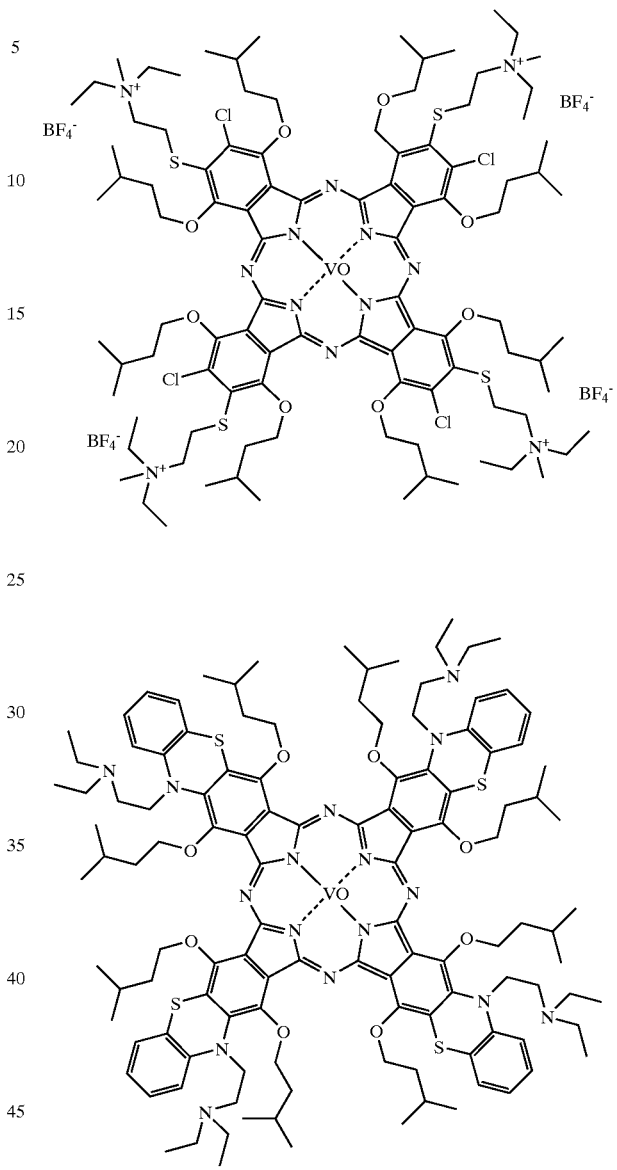

In formula (e), $R^{35}$ to $R^{50}$ each independently represent a hydrogen atom, a halogen atom, a cyano group, an alkyl group, an aryl group, a alkenyl group, an alkynyl group, a hydroxyl group, a carbonyl group, a thio group, a sulfonyl group, a sulfinyl group, an oxy group, an amino group, or an onium salt structure. Each of $R^{35}$ to $R^{50}$ may have a substituent. M represents two hydrogen atoms, or a metal atom, a halometal group or an oxymetal group, in which the metal atom includes atoms of the Groups IA, IIA, IIIB and IVB, and transition metals and lanthanoid elements of the Periods 1, 2 and 3 of the Periodic Table. Of those, especially preferred are copper, magnesium, iron, zinc, cobalt, aluminium, titanium and vanadium.

The pigments which is used as a light-heat converting agent in the present invention may be any of commercially-available pigments and any of other known pigments, for example, those described in *Color Index (C.I.) Handbook; Latest Pigment Handbook* (the Pigment Technology Association of Japan, 1977); *Latest Pigment Application Technology* (CMC, 1986); and *Printing Ink Technology* (CMC, 1984).

Various types of pigments are usable herein, including, for example, black pigments, yellow pigments, orange pigments, brown pigments, red pigments, violet pigments, blue pigments, green pigments, fluorescent pigments, metal powder pigments, and polymer-bonded pigments. Specifically, examples include insoluble azo pigments, azo-lake pigments, condensed azo pigments, chelate-azo pigments, phthalocyanine pigments, anthraquinone pigments, perylene and perinone pigments, thioindigo pigments, quinacridone pigments, dioxazine pigments, isoindolinone pigments, quinophthalone pigments, dyed lake pigments, azine pigments, nitroso pigments, nitro pigments, natural pigments, fluorescent pigments, inorganic pigments, and carbon black. Of these, carbon black is preferred.

These pigments may be used without being surface-treated, or may be surface-treated. Surface treatments include a method of coating the surface with resin or wax; a method of adhering a surfactant; and a method of bonding a reactive substance (e.g., a silane coupling agent, epoxy compound, or polyisocyanate) to the surface. The methods of surface treatment as above are described in *Properties and Applications of Metal Soap* (Miyuki Publishing); *Printing Ink Technology* (CMC, 1984); and *Latest Pigment Application Technology* (CMC, 1986).

Preferably, the IR absorbent is in the image-recording material in an amount of 0.01 to 50% by weight, preferably from 0.1 to 20% by weight, even more preferably from 1 to 10% by weight of the total solid content of the material. If the amount of the IR absorbent in the material is smaller than 0.01% by weight, the sensitivity of the material will be low; but if larger than 50% by weight, the non-image area of printed matters will be stained.

Preferably, the optical density of the recording material that contains the IR absorbent as above falls between 0.05 and 3.0 at the absorption peak in the IR range. If the optical density thereof oversteps the range, the sensitivity of the recording material may be low. The optical density is determined, based on the amount of the IR absorbent in the recording material and the thickness of the recording layer of the material. Therefore, the desired optical density may be attained by controlling the condition of the two. The optical density of the recording layer may be measured in any ordinary manner. For example, the recording material of which the optical density is to be measured is applied to a transparent or white support to form thereon a recording layer of which the dry thickness is defined within the range necessary for planographic printing plates, and the transmittance of the recording layer is measured with a transmission densitometer; or it is applied to a reflective support of, for example, aluminium to form thereon a recording layer, and the reflection density of the layer is measured.

The IR absorbent may be added to one and the same photosensitive layer of the recording material along with the other components; or it maybe in a separate layer, and the layer containing the IR absorbent may be combined with other layers containing the other components.

(B) Radical Generator

The radical generator is a compound that generates a radical after having received optical and/or thermal energy, and initiates and promotes the polymerization of polymerizable unsaturated group-having compounds. The radical initiator for use in the invention may be any known thermal polymerization initiator or any known compound requiring small bond-dissociation energy. For example, it includes onium salts, trihalomethyl group-having triazine compounds, peroxides, azo-type polymerization initiators, azide compounds, quinonediazide compounds, metallocene compounds, organoboron salt compounds. Preferred for it are onium salts mentioned below, as having high sensitivity.

Preferred onium salts for use as the radical generator in the invention are diazonium salts, iodonium salts, sulfonium salts, ammonium salts, and pyridinium salts. Of those, more preferred are iodonium salts, diazonium salts and sulfonium salts. The onium salts are not acid generators, but function as an ionic radical polymerization initiator. Preferred onium salts for use in the invention are those of the following general formulae (III) to (V):

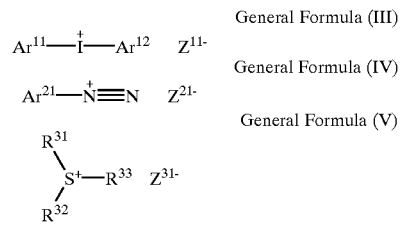

In general formula (III), $Ar^{11}$ and $Ar^{12}$ each independently represent an optionally-substituted aryl group having at most 20 carbon atoms. Preferred examples of substituents therefor include a halogen atom, a nitro group, an alkyl group having at most 12 carbon atoms, an alkoxy group having at most 12 carbon atoms, and an aryloxy group having at most 12 carbon atoms. $Z^{11-}$ represents a counter ion selected from the group consisting of halide ions, perchlorate ions, tetrafluoroborate ions, hexafluorophosphate ions, carboxylate ions and sulfonate ions, and is preferably any of perchlorate ions, hexafluorophosphate ions, carboxylate ions and arylsulfonate ions.

In general formula (IV), $Ar^{21}$ represents an optionally-substituted aryl group having at most 20 carbon atoms. Preferred substituents include a halogen atom, a nitro group, an alkyl group having at most 12 carbon atoms, an alkoxy group having at most 12 carbon atoms, an aryloxy group having at most 12 carbon atoms, an alkylamino group having at most 12 carbon atoms, a dialkylamino group having at most 12 carbon atoms, an arylamino group having at most 12 carbon atoms, and a diarylamino group having at most 12 carbon atoms. $Z^{21-}$ has the same meaning as $Z^{11-}$, representing a counter ion.

In formula (V), $R^{31}$, $R^{32}$ and $R^{33}$ may be the same or different, and each represent an optionally-substituted hydrocarbon group having at most 20 carbon atoms. Preferred substituents for them are a halogen atom, a nitro group, an alkyl group having at most 12 carbon atoms, an alkoxy group having at most 12 carbon atoms, and an aryloxy group having at most 12 carbon atoms. $Z^{31-}$ has the same meaning as $Z^{11-}$, representing a counter ion.

Hereinunder shown are specific examples of preferred onium salts for use in the present invention, those of formula (III) are [OI-1] to [OI-10], those of formula (IV) are [ON-1] to [ON-5], and those of formula (V) are [OS-1] to [OS-7].

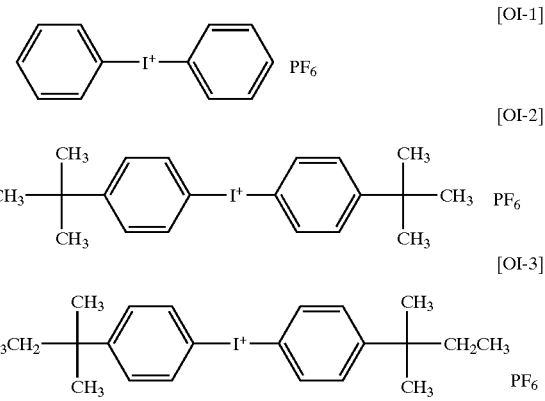

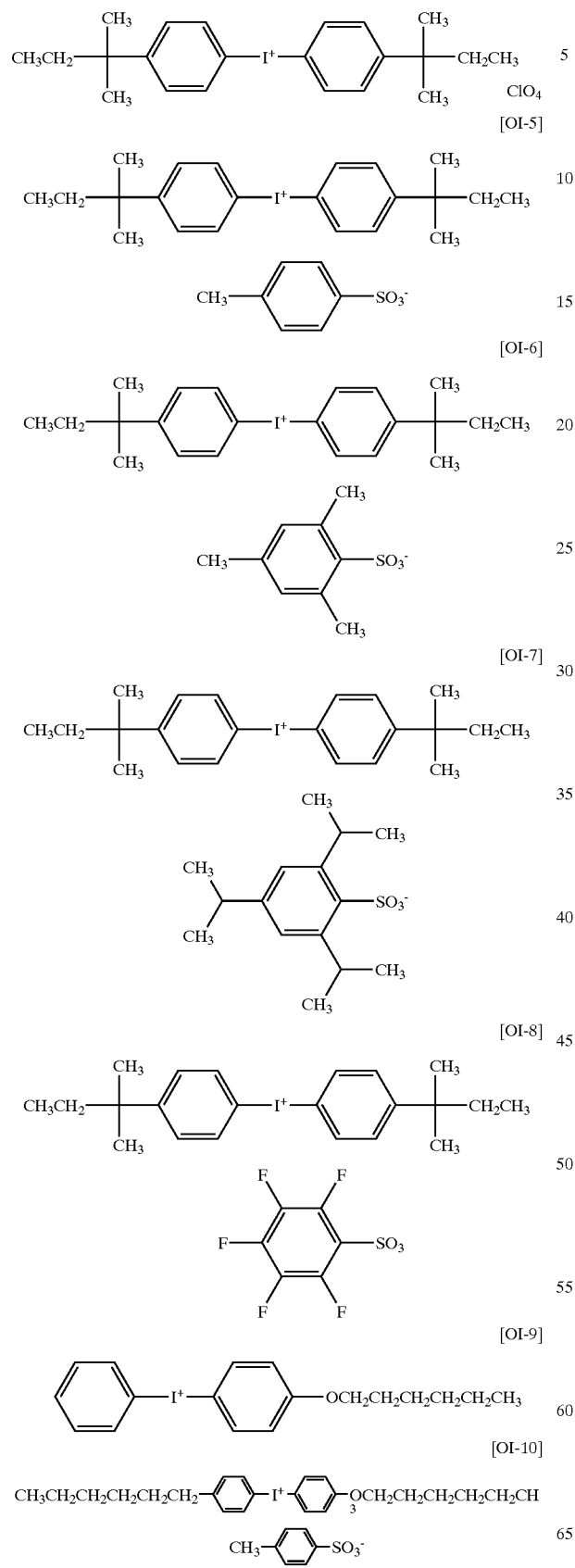
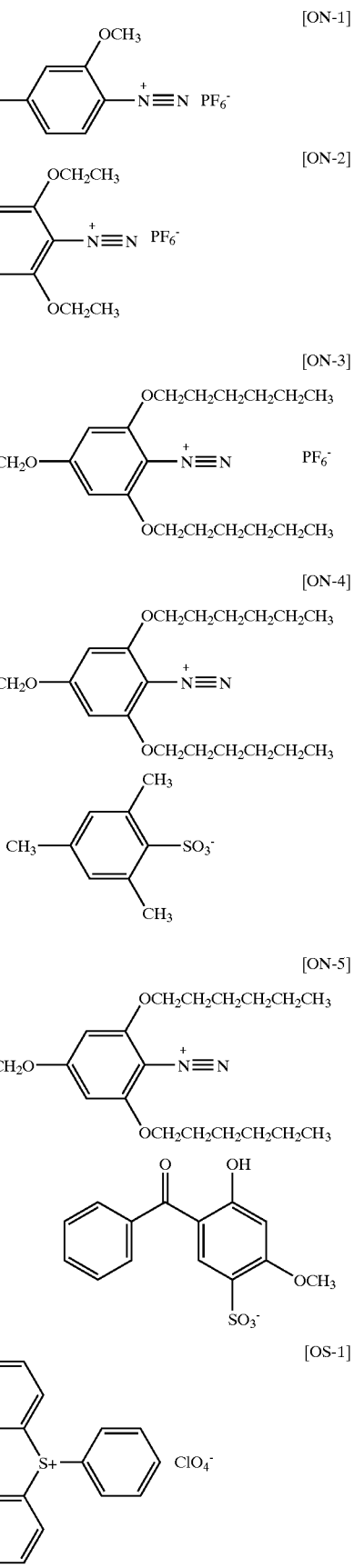

[OS-2] 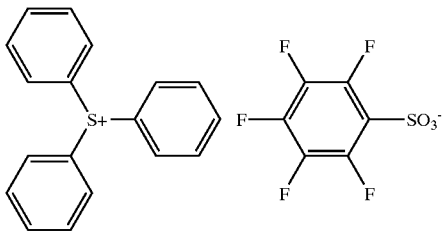

[OS-3]

[OS-4]

[OS-5] 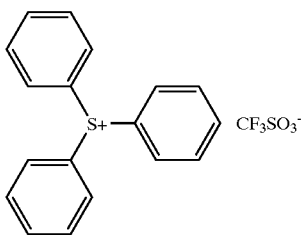

[OS-6] 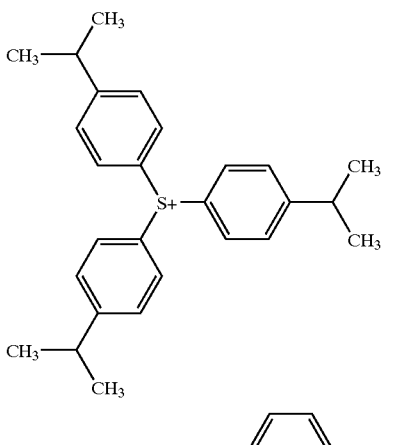

[OS-7] 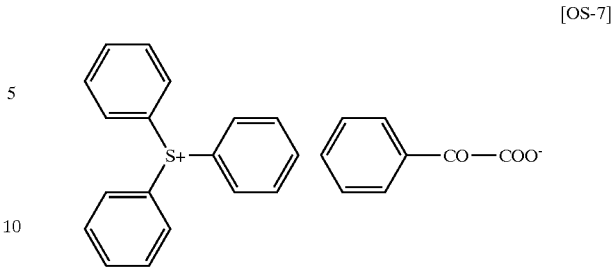

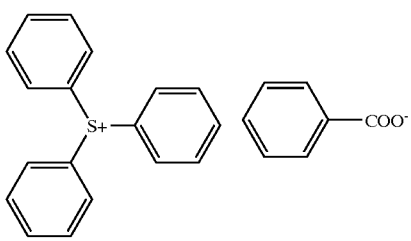

Preferably, the radical generator for use in the invention has a peak absorption wavelength of not longer than 400 nm, more preferably not longer than 360 nm. As the radical generator therein has the absorption wavelength in the UV range, the image-recording material of the invention can be handled and processed even under white light.

The radical generator may be in the image-recording material in an amount of from 0.1 to 50% by weight, preferably from 0.5 to 30% by weight, more preferably from 1 to 20% by weight of the total solid content of the material. If the amount of the radical generator therein is smaller than 0.1% by weight, the sensitivity of the recording material will be low; but if larger than 50% by weight, the non-image area of printed matters will be stained. One or more such radical generators may be in the recording material either singly or as combined. If desired, the radical generator may be added to one and the same photosensitive layer of the material along with the other components; or it may be in a separate layer, and the layer containing the radical generator may be combined with others layers containing the other components.

(C) Radically-polymerizable Compound

The radically-polymerizable compound in the image-recording material of the present invention has at least one ethylenically unsaturated double bond, and is selected from compounds having at least one, preferably at least two terminal ethylenically unsaturated bonds. These compounds are well known in the art, and any of them are usable herein with no specific limitation. They have various chemical forms, including, for example, monomers, prepolymers (e.g., dimers, trimers and oligomers), and mixtures and copolymers thereof and the like. Examples of monomers and copolymers thereof are unsaturated carboxylic acids (e.g., acrylic acid, methacrylic acid, itaconic acid, crotonic acid, isocrotonic acid, maleic acid and the like), and esters and amides thereof. Preferred are esters of unsaturated carboxylic acids and aliphatic polyalcohols; and amides of unsaturated carboxylic acids and aliphatic polyamines. Also preferred are adducts of unsaturated carboxylates or amides having a nucleophilic substituent of, for example, a hydroxyl, amino or mercapto group, with monofunctional or polyfunctional isocyanates or epoxides; and dehydrated condensates thereof with monofunctional or polyfunctional carboxylic acids. Also preferred are adducts of unsaturated carboxylates or amides having an electrophilic substituent of, for example, an isocyanate or epoxy group, with monofunctional or polyfunctional alcohols, amines or thiols; and substituting reaction products of unsaturated carboxylates or amides having a leaving substituent of, for example, a halogen or a tosyloxy group, with monofunctional or polyfunctional alcohols, amines or thiols. Also usable herein are other groups of compounds, for which unsaturated phosphonic acids or styrenes are used in place of the unsaturated carboxylic acids.

Specific examples of esters of aliphatic polyalcohols and unsaturated carboxylic acids for use as the radically-polymerizable compound are mentioned below. Acrylates include ethylene glycol diacrylate, triethylene glycol diacrylate, 1,3-butanediol diacrylate, tetramethylene glycol diacrylate, propylene glycol diacrylate, neopentyl glycol diacrylate, trimethylolpropane triacrylate, trimethylolpropane tri(acryloyloxypropyl) ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl) isocyanurate, polyester acrylate oligomers and the like.

Methacrylates include tetramethylene glycol dimethacrylate, triethylene glycol di-methacrylate, neopentyl glycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl]dimethylmethane, bis-[p-(methacryloxyethoxy)phenyl]dimethylmethane and the like.

Itaconates include ethylene glycol diitaconate, propylene glycol diitaconate, 1,3-butanediol diitaconate, 1,4-butanediol diitaconate, tetramethylene glycol diitaconate, pentaerythritol diitaconate, sorbitol tetraitaconate and the like.

Crotonates include ethylene glycol dicrotonate, tetramethylene glycol dicrotonate, pentaerythritol dicrotonate, sorbitol tetracrotonate and the like.

Isocrotonates include ethylene glycol diisocrotonate, pentaerythritol diisocrotonate, sorbitol tetraisocrotonate and the like.

Maleates include ethylene glycol dimaleate, triethylene glycol dimaleate, pentaerythritol dimaleate, sorbitol tetramaleate and the like.

Other esters also preferred for use herein are, for example, aliphatic alcohol esters such as those described in JP-B Nos. 46-27926 and 51-47334, and JP-A No. 57-196231; aromatic esters as in JP-A Nos. 59-5240, 59-5241 and 2-226149; and amino-having esters as in JP-A No. 1-165613.

Specific examples of amide monomers of aliphatic polyamines and unsaturated carboxylic acids preferred for use herein are methylenebis-acrylamide, methylenebis-methacrylamide, 1,6-hexamethylenebis-acrylamide, 1,6-hexamethylenebis-methacrylamide, diethylenetriamine-trisacrylamide, xylylenebis-acrylamide, xylylenebis-methacrylamide and the like.

Other amide monomers also preferred for use herein are those having a cyclohexylene structure, as in JP-B No. 54-21726.

Also preferred are urethane polyadducts obtained through addition reaction of isocyanates with hydroxyl compounds. Specific examples are vinylurethanes having at least two polymerizable vinyl groups in one molecule, which are produced through addition reaction of polyisocyanate compounds having at least two isocyanate groups in one molecule with hydroxyl-having vinyl monomers of the following formula (VI) and the like, for example, as in JP-B No. 48-41708.

$$CH_2=C(R^{41})COOCH_2CH(R^{42})OH \quad \text{General formula (VI)}$$

wherein $R^{41}$ and $R^{42}$ each represent H or $CH_3$.

Also preferred for use herein are urethane acrylates such as those described in JP-A No. 51-37193, and JP-B Nos. 2-32293 and 2-16765; and ethylene oxide skeleton-having urethane compounds as in JP-B Nos. 58-49860, 56-17654, 62-39417 and 62-39418.

Also usable herein are radically-polymerizable compounds having an amino structure or sulfido structure in the molecule, such as those described in JP-A Nos. 63-277653, 63-260909 and 1-105238.

Other examples usable herein are polyfunctional acrylates and methacrylates such as polyester acrylates, and epoxy acrylates produced through reaction of epoxy resins with (meth)acrylic acids, for example, as in JP-A No. 48-64183, and JP-B Nos. 49-43191 and 52-30490. Also usable are specific unsaturated compounds, as in JP-B Nos. 46-43946, 1-40337 and 1-40336; and vinylphosphonic acids, as in JP-A No. 2-25493. As the case may be, preferred are perfluoroalkyl-having compounds such as those described in JP-A No. 61-22048. Also usable herein are photo-curable monomers and oligomers disclosed in *Journal of the Adhesive Association of Japan*, Vol. 20, No. 7. pp. 300–308 (1984).

Details of the use of these radically-polymerizable compounds in the present invention, including what type of compound is used, whether the compounds are used singly or combined, and how much of the compound is added to the recording material, may be freely determined in accordance with the performance requirements of the ultimate recording material of the present invention. For example, the compounds may be selected in view of the following points. With respect to the sensitivity of the recording material, preferred are radically-polymerizable compounds having more unsaturated groups in one molecule. In many cases, preferred are polyfunctional compounds that are at least difunctional. On the other hand, in order to increase the mechanical strength of the image area, that is, the mechanical strength of the cured film of the material, preferred are polyfunctional compounds that are at least trifunctional. Combining various radically-polymerizable compounds that differ in the number of functional groups therein and in the type of polymerizable groups therein (for example, acrylates, methacrylates, styrenes and the like) is effective for enhancing both the sensitivity of the recording material and the mechanical strength of the image area of the film of the material. Compounds having a large molecular weight and compounds having a high degree of hydrophobicity ensure high sensitivity and high film strength, but are often undesirable as they might not be well processed at high development speed and as they often deposit in developers. Selection and use of radically-polymerizable compounds in the present invention is a matter of great importance in view of their compatibility and dispersibility with the other components of the photosensitive layer of the recording material of the present invention (e.g., binder polymers, polymerization initiators and colorants). For example, using low-purity compounds or combining two or more different compounds may improve the compatibility of the compounds with the other components. As the case may be, compounds having a specific structure can be selected for improving adhesiveness of the recording material to a support or overcoat layer. In general, the blend ratio of the radically-polymerizable compound in the recording layer of the image-recording material is preferably larger for higher sensitivity of the image-recording layer. However, if the blend ratio is too large, there may be problems in that unfavorable phase separation may occur in the coating liquid of the material, the image-recording layer of the material may be sticky and interfere with smooth production of products (for example, the components of the recording layer are transferred and adhere to unintended areas), and deposits may be formed in a developer solution. In view of these points, the preferred blend ratio of the radically-polymerizable material in the recording material of the present invention is generally from 5 to 80% by weight, more preferably between 20 and 75% by weight of all the components of the material. One or more different radically-polymerizable compounds may be in the material either singly or combined. Regarding a method of using the radically-polymerizable compounds in the material, the structure, the blend ratio and the amount of the compounds to be in the material may be suitably selected depending on a degree of polymerization retardation of the compounds by oxygen, resolution of the recording layer containing the compound, fogging resistance, a refractive index change, surface adhesiveness and the like. As the case may be, subbing layers or over-coat layers may be disposed on or below the recording layer in any desired manner.

(D) Binder Polymer:

The image-recording material of the present invention may contain a binder polymer for improving film characteristics of the recording layer of the material. As the binder, preferred are linear organic polymers. A linear organic polymer for use in the present invention may be any known linear organic polymer. Preferred are those soluble or swellable in water or weakly alkaline water, for enabling development of the material with water or weakly alkaline water. The linear organic polymer serving as a film-forming agent in the image-recording material may be selected depending on the mode of development of the material with one of water, weak alkaline water or a solvent developer. For example, if a water-soluble organic polymer is used, the recording material can be developed with water. The linear organic polymers may be radical polymers having a carboxylic acid group in the side branches, such as those described in JP-A No. 59-44615, JP-B Nos. 54-34327, 58-12577 and 54-25957, and JP-A Nos. 54-92723, 59-53836 and 59-71048. These include, for example, methacrylic acid copolymers, acrylic acid copolymers, itaconic acid copolymers, crotonic acid copolymers, maleic acid copolymers, and partial esters of maleic acid copolymers. In addition to these, also usable herein are acid cellulose derivatives having a carboxylic acid group in the side branches, as well as hydroxyl-having polymer adducts with cyclic acid anhydrides.

Of these, especially preferred are (meth)acrylic resins having both a benzyl or allyl group and a carboxyl group in the side branches and alkali-soluble resins having a double bond in the side chain as described in JP-A 2000-187322, due to ensuring good balance of the film strength, the sensitivity and the developability of the image-recording material.

Also preferred are urethane-type binder polymers having an acid group, such as those described in JP-B Nos. 7-12004, 7-120041, 7-120042 and 8-12424, JP-A Nos. 63-287944, 63-287947 and 1-271741, and Japanese Patent Application No. 10-116232, due to ensuring extremely high strength of the image-recording layer of the material, and therefore ensuring good printing durability of the processed material and good low-exposure latitude in processing the material.

In addition, polyvinyl pyrrolidone, polyethylene oxide and the like are also preferred for water-soluble linear organic polymers for use herein. Also preferred are alcohol-soluble nylons and polyethers of 2,2-bis (4-hydroxyphenyl) propane and epichlorohydrin, for increasing the mechanical strength of the cured film of the recording material.

Preferably, the polymer used in the present invention has a weight-average molecular weight of at least 5,000, more preferably from 10,000 to 300,000, and a number-average molecular weight of at least 1,000, more preferably from 2,000 to 250,000. Also, the polymer preferably has a molecular weight distribution (weight-average molecular weight/number-average molecular weight) of at least 1, more preferably from 1.1 to 10.

The polymer may be any of random polymers, block polymers and graft polymers, but is preferably a random polymer.

The polymer for use in the present invention may be synthesized by any known method. Solvents usable in synthesis include, for example, tetrahydrofuran, ethylene dichloride, cyclohexanone, methyl ethyl ketone, acetone, methanol, ethanol, ethylene glycol monomethyl ether, ethylene glycol monoethyl ether, 2-methoxyethyl acetate, diethylene glycol dimethyl ether, 1-methoxy-2-propanol, 1-methoxy-2-propyl acetate, N,N-dimethylformamide, N,N-dimethylacetamide, toluene, ethyl acetate, methyl lactate, ethyl lactate, dimethylsulfoxide, and water. One or more of these solvents may be used either singly or as combined.

A radical polymerization initiator usable for synthesizing the polymer may be any known compound, including, for example, azo-type initiators, and peroxide initiators.

In producing the image-recording material of the present invention, one or more binder polymers may be added thereto either singly or combined. Preferably, the amount of polymer to be added to the material is from 20 to 95% by weight, more preferably between 30 and 90% by weight of total solid content of the material. If the amount is smaller than 20% by weight, adding the polymer will be ineffective for increasing mechanical strength of the image area of the film of the processed material; but if larger than 95% by weight, no image will be formed on the material. Also, preferably, the ratio of the binder polymer, that is, the linear organic polymer, to the radically-polymerizable ethylenically unsaturated double bond-having compound, which is essential component (C) in the recording material, is from 1/9 to 7/3 by weight.

Other Components

In addition to the components mentioned above, various compounds may be optionally added to the image-recording material of the present invention. For example, dyes having a great absorption in the visible light range may be added thereto, serving as colorants for images. Specifically, the dyes are Oil Yellow #101, Oil Yellow #103, Oil Pink #312, Oil Green BG, Oil Blue BOS, Oil Blue #603, Oil Black BY, Oil Black BS, Oil Black T-505 (these are products of Orient Chemical); Victoria Pure Blue, Crystal Violet (CI 42555), Methyl Violet (CI 42535), Ethyl Violet, Rhodamine B (CI 145170B), Malachite Green (CI 42000), Methylene Blue (CI 52015), dyes described in JP-A No. 62-293247, and the like. Pigments such as phthalocyanine pigments, azo pigments, carbon black and titanium oxide are also preferred as colorants for the recording material.

Adding the colorant to the image-recording material is preferred, due to facilitating differentiation of the image area from the non-image area in the layer of the processed material. The amount of the colorant in the material may fall between 0.01 and 10% by weight of the total solid content of the material.

Preferably, a small amount of a thermal polymerization inhibitor is added to the image-recording material for preventing unnecessary thermal polymerization of the radically-polymerizable, ethylenically unsaturated double bond-having compound in the material while the material is being produced or stored. Examples of the thermal polymerization inhibitor are hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitroso-N-phenylhydroxylamine aluminium salt and the like. Preferably, the amount of the thermal polymerization inhibitor in the material falls between about 0.01% by weight and about 5% by weight of the material. If desired, a higher fatty acid or derivative thereof, such as behenic acid or behenic acid amide, having the ability to prevent polymerization retardation by oxygen may be added to the recording material. In a step of drying the material after coating on a support, the acid or acid derivative added to the material may be localized in the surface of the photosensitive layer of the material formed on the support. Preferably, the amount of the higher fatty acid or derivative in the recording material falls between about 0.1% by weight and about 10% by weight of the material.

Also, the image-recording material of the present invention may contain a nonionic surfactant, as in JP-A Nos. 62-251740 and 3-208514, or an ampholytic surfactant as in JP-A Nos. 59-121044 and 4-13149, for further ensuring stable development of the material in various conditions.

Specific examples of the nonionic surfactant are sorbitan tristearate, sorbitan monopalmitate, sorbitan trioleate, stearic acid monoglyceride, polyoxyethylene nonylphenyl ether and the like.

Specific examples of the ampholytic surfactant are alkyl-di(aminoethyl)glycines, alkyl-polyaminoethylglycine hydrochlorides, 2-alkyl-N-carboxyethyl-N-hydroxyethylimidazolinium betaines, N-tetradecyl-N,N-betaines (e.g., AMOGEN K manufactured by Dai-ichi Kogyo) and the like.

The amount of the nonionic surfactant or ampholytic surfactant in the image-recording material preferably falls between 0.05 and 15% by weight, more preferably between 0.1 and 5% by weight of the material.

Also, if desired, the image-recording material of the present invention may contain a plasticizer for softening the film of the material. The plasticizer includes, for example, polyethylene glycol, tributyl citrate, diethyl phthalate, dibutyl phthalate, dihexyl phthalate, dioctyl phthalate, tricresyl phosphate, tributyl phosphate, trioctyl phosphate, tetrahydrofurfuryl oleate or the like.

In general, the above-mentioned components of the image-recording material of the present invention are dissolved in a solvent and applied to a suitable support. The solvent includes, for example, ethylene dichloride, cyclohexanone, methyl ethyl ketone, methanol, ethanol, propanol, ethylene glycol monomethyl ether, 1-methoxy-2-propanol, 2-methoxyethyl acetate, 1-methoxy-2-propyl acetate, dimethoxyethane, methyl lactate; ethyl lactate, N,N-dimethylacetamide, N,N-dimethylformamide, tetramethylurea, N-methylpyrrolidone, dimethylsulfoxide, sulforane, γ-butyrolactone, toluene, water or the like, but is not limited thereto. These solvents may be used singly or combined. Preferably, the concentration of the constituent components (in terms of total solid content including additives) in the solvent falls between 1 and 50% by weight.

The amount (in terms of solid content of the material) of the layer formed and dried on the support varies depending on the use of the material, but in general is preferably between 0.5 and 5.0 g/m$^2$ for planographic printing plates. For applying the coating liquid of the material to supports, various coating methods can be employed. For example, employable are any of bar coating, spin coating, spraying, curtain coating, dipping, air-knife coating, blade coating, and roll coating. With a decrease in the amount of the material coated, the apparent sensitivity of the image-recording layer formed increases, but the film characteristics of the layer decrease.

For improving the coatability of the image-recording material of the present invention, a surfactant, for example, a fluorine-containing surfactant as in JP-A No. 62-170950 may be added to the material. Preferably, the amount of the surfactant to be added falls between 0.01 and 1% by weight, and more preferably between 0.05 and 0.5% by weight of the total content of the material.

Resin Interlayer

In the image-recording material of the invention, a resin interlayer may be provided, if desired, between the recording layer that contains a photopolymerizable compound and the support.

In the image-recording material having the resin interlayer, the photopolymerizable compound-containing, IR-sensitive recording layer of which the solubility in an alkali developer reduces after exposure to IR rays may be shifted nearer to the light-receiving face or therearound of the material, and therefore the sensitivity of the recording layer to IR laser is thereby increased. In addition, in the recording material, the resin interlayer of a polymer substance existing between the support and the IR-sensitive recording layer functions as a heat-insulating layer, and therefore the heat generated through exposure of the material to IR laser is efficiently transferred to the recording layer, not diffusing into the support. In the exposed area of the material, the IR-sensitive layer having changed impervious to alkali developer functions as a protective layer for the resin interlayer, and therefore, the development stability of the material is enhanced. As a result, images of good discrimination can be formed in the processed material, and, in addition; the storage stability of the processed material may be enhanced. In the non-exposed area of the recording material, the non-cured binder component rapidly dissolves and disperses in developer. In addition, since the resin interlayer adjacent to the support comprises an alkali-soluble polymer substance, it well dissolves in developer. For example, even if a developer of lowered activity is used for processing the recording material, the layer in the non-exposed area can rapidly dissolve therein, not interfering with the developability of the material.

Protective Layer

On the recording layer of the image-recording material of the invention that contains a photopolymerizable compound, optionally formed is a protective layer. The planographic printing plate of this type is generally exposed to light in air. The protective layer formed on the photosensitive layer acts to prevent low-molecular compounds such as oxygen and basic substances from entering the photosensitive layer (these low-molecular compounds are present in air and retard image formation in the photosensitive layer exposed to light in air), and thereby protects the photosensitive layer from such low-molecular compounds. Accordingly, the necessary characteristic of the protective layer is that oxygen and other low-molecular compounds do not permeate through the layer. In addition, it is desirable that the light transmission through the layer is high, the adhesiveness of the layer to the underlying photosensitive layer is good, and the protective layer is readily removed through development after exposure.

Various protective layers have heretofore been suggested, for example, as described in detail in U.S. Pat. No. 3,458,311 and JP-A No. 55-49729. For a material for the protective layer preferred is, for example, a water-soluble polymer compound having a relatively high degree of crystallinity. Specifically known are water-soluble polymers such as polyvinyl alcohol, polyvinyl pyrrolidone, acetic cellulose, gelatin, gum arabic, and polyacrylic acid. Of those, polyvinyl alcohol is preferred as a main component of the protective layer, due to providing the best results for basic characteristics of a layer that blocks out oxygen and is readily removable through development. Polyvinyl alcohol for the protective layer may be partially esterified, etherified and/or acetallized as long as it has unsubstituted vinyl alcohol units, which are necessary for its oxygen barrier property and for its solubility in water. Also, if desired, a part thereof may have another copolymer component.

For example, polyvinyl alcohol hydrolyzed to a degree of from 71 to 100% and having a molecular weight of from 300 to 2,400 maybe used for the protective layer. Specific examples of polyvinyl alcohol of this type are Kuraray's PVA-105, PVA-110, PVA-117, PVA-117H, PVA-120, PVA-124, PVA-124H, PVA-CS, PVA-CST, PVA-HC, PVA-203, PVA-204, PVA-205, PVA-210, PVA-217, PVA-220, PVA-224, PVA-217EE, PVA-217E, PVA-220E, PVA-224E, PVA-405, PVA-420, PVA-613 and L-8 and the like.

The constituent components of the protective layer (e.g., the type of PVA to be used, the presence or absence of additives in the layer), and the amount forming the layer should be determined in consideration of the oxygen barrier property of the layer, the removability of the layer through development, and also fogging resistance, adhesiveness and scratch resistance of the layer. In general, PVA hydrolyzed to a higher degree (PVA in which unsubstituted vinyl alcohol units are higher in number) and a thicker protective layer are effective for higher oxygen barrier property of the layer and higher sensitivity. However, it is often problematic if the ability of the protective layer to block out oxygen is enhanced too much, in that some unnecessary polymerization will occur in the photosensitive recording layer while photographic materials comprising the layer are produced or are stored before processing, and that, when imagewise exposed, the layer will be undesirably fogged or an image line formed in exposure will be thickened. In addition, the adhesiveness of the protective layer to the image area of the processed photosensitive layer and the scratch resistance of the protective layer are also extremely important in handling the printing plates. Specifically, when a hydrophilic layer of a water-soluble polymer (the protective layer of this case) is laminated over an oleophilic polymerizing layer (the photosensitive recording layer), the hydrophilic polymer layer tends to peel off from the oleophilic polymerizing layer as adhesiveness between the two is low. In this case, the part of the oleophilic polymerizing layer (photosensitive recording layer) from which the hydrophilic polymer layer (protective layer) has been peeled will not be well polymerized owing to oxygen penetration thereinto, and will therefore involve a defect of curing failure.

To solve this problem, that is, to improve the adhesiveness between the two layers, various proposals have heretofore been made. For example, in U.S. Pat. No. 4,072,527, from 20 to 60% by weight of an acrylic emulsion or a water-insoluble vinyl pyrrolidone-vinyl acetate copolymer is added to a hydrophilic polymer essentially of polyvinyl alcohol, and a layer of the resulting mixture is laminated over a polymerizing layer to ensure good adhesiveness between the two layers. Any known technique, such as that disclosed in these US patent specifications, may be applied to the protective layer in the present invention. Methods of forming the protective layer in such a known manner are described in detail in, for example, U.S. Pat. No. 3,458,311 and JP-A No. 55-49729.

Further, the protective layer may be modified to provide additional functions. For example, a colorant (e.g., a water-soluble dye) capable of transmitting light for exposure (for example, IR radiation in a wavelength range of about from 760 to 1200 nm for the image-recording material of the present invention) and capable of efficiently absorbing other light, which does not participate in exposure, may be added to the protective layer to thereby further broaden safe light latitude of the photographic material having the protective layer, while not lowering the sensitivity.

Support

One example of a support to which the image-recording material of the present invention may be applied is a tabular support having good dimensional stability, for example, paper, paper laminated with a plastic material (e.g., polyethylene, polypropylene or polystyrene), metal sheets (of, for example, aluminium, zinc or copper), plastic films (of, for example, cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate, or polyvinyl acetal), or paper or plastic films coated with metal, such as the metals mentioned above, through lamination or deposition.

As the support of the image-recording material of the present invention, preferred are polyester films and aluminium sheets. Above all, especially preferred are aluminium sheets, due to having good dimensional stability and being relatively inexpensive. Preferably, the aluminium sheet is a pure aluminium sheet or an aluminium alloy consisting mainly of aluminium and containing traces of hetero elements. Aluminium-laminated or deposited plastic films are also usable herein. The hetero elements in the aluminium alloy include, for example, silicon, iron, manganese, copper, magnesium, chromium, zinc, bismuth, nickel and titanium. The hetero element content of the aluminium alloy is at most 10% by weight. Especially preferred for use in the present invention are pure aluminium sheets. However, completely pure aluminium is difficult to prepare with an ordinary smelting technique. Therefore, the aluminium for use herein may contain traces of hetero elements. The aluminium sheets for use in the present invention are not specifically defined with regard to composition, and any known aluminium sheets which have been used in the art may be used in the present invention. The thickness of the aluminium sheet may be from 0.1 mm to 0.6 mm or so, preferably between 0.15 mm and 0.4 mm, and more preferably between 0.2 mm and 0.3 mm.

Prior to roughening, if desired, the surface of the aluminium sheet may be degreased, for example, by treatment with a surfactant, an organic solvent or an aqueous alkali solution, for removing rolling oil.

The surface of the aluminium sheet may be roughened by various methods. For example, it may be mechanically roughened, or maybe roughened through electrochemical surface dissolution or through selective chemical dissolution. For mechanical roughening, any known method is employable. For example, the surface of the aluminium sheet may be roughened by ball grinding, brushing, blasting, or buffing. For electrochemical roughening, for example, the aluminium sheet may be processed in an electrolytic solution of hydrochloric acid or nitric acid with a direct current or an alternating current being applied. These two methods may be combined, as in JP-A No. 54-63902.

If desired, the thus-roughened aluminium sheet may be etched with alkali and neutralized, and then optionally subjected to anodic oxidation for further enhancing water retentiveness and abrasion resistance of the surface. For anodic oxidation of the aluminium sheet, employable are various types of electrolytes capable of forming porous oxide films. Generally employed is sulfuric acid, phosphoric acid, oxalic acid, chromic acid or a mixture thereof. The concentration of the electrolyte for anoxic oxidation may be determined depending on the type of the electrolyte used.

The conditions for anodic oxidation vary, depending on the type of the electrolyte used, and therefore cannot be specified for all cases. In general, however, electrolyte concentration of the processing solution may be between 1 and 80% by weight; temperature of the processing solution may be between 5 and 70° C.; current density may be between 5 and 60 A/dm$^2$; voltage may be between 1 and 100 V; and the time for electrolysis may be between 10 seconds and 5 minutes.

The amount of the oxide film to be formed through such anodic oxidation is preferably at least 1.0 g/m$^2$. If the amount is less, desired printing durability will be unsatisfactory, and the non-image area of the planographic printing plate will be readily scratched. After scratching, ink will adhere to the scratches and obtained prints will often be stained.

After having been subjected to anodic oxidation, the surface of the aluminium sheet is optionally hydrophilicated. For hydrophilication, employable is, for example, a method of processing the aluminium sheet with an alkali metal silicate (e.g., aqueous sodium silicate solution), as in U.S. Pat. Nos. 2,714,066, 3,181,461, 3,280,734 and 3,902,734. In this method, the support is dipped in an aqueous sodium silicate solution or is electrolyzed in the solution. Apart from this method, also employable is a method of processing the aluminium sheet with potassium fluorozirconate, as in JP-B No. 36-22063; or a method of processing with polyvinylphosphonic acid, as in U.S. Pat. Nos. 3,276,868, 4,153,461 and 4,689,272.

The image-recording material of the present invention may be applied to a support such as that mentioned hereinabove, to form thereon a recording layer of the material. If desired, a subbing layer may be provided between the recording layer and the support.

Various organic compounds can be used as components of the subbing layer. For example, carboxymethyl cellulose, dextrin, gum arabic; amino group-having phosphonic acids such as 2-aminoethylphosphonic acid; other organic phosphonic acids such as optionally-substituted phenylphosphonic acids, naphthylphosphonic acids, alkylphosphonic acids, glycerophosphonic acids, methylenediphosphonic acids and ethylenediphosphonic acids; organic phosphoric acids such as optionally-substituted phenylphosphoric acid, naphthylphosphoric acid, alkylphosphoric acid and glycerophosphoric acid; organic phosphinic acids such as optionally-substituted phenylphosphinic acid, naphthylphosphinic acid, alkylphosphinic acid and glycerophosphinic acid; amino acids such as glycine and β-alanine; and hydroxyl group-having amine hydrochlorides such as triethanolamine hydrochloride and the like. Two or more of these compounds may be combined as components of the subbing layer.

After the support has been processed and/or coated with a subbing layer as above, a back surface of the support is optionally coated with a back coat layer. For the back coat layer, preferred are organic polymer compounds such as those described in JP-A No. 5-45885; and metal oxides formed by hydrolyzing and polycondensing organic or inorganic metal compounds, such as described in JP-A No. 6-35174. More preferred are silicon alkoxides such as Si(OCH$_3$)$_4$, Si(OC$_2$H$_5$)$_4$, Si(OC$_3$H$_7$)$_4$, and Si(OC$_4$H$_9$)$_4$, which are inexpensive and easily available. Especially preferred are coating layers of such metal oxides, which are highly resistant to developers.

One preferred characteristic of the support for the planographic printing plate is that surface roughness thereof is between 0.10 and 1.2 μm in terms of center line average height. If this is lower than 0.10 μm, the adhesiveness between the support and the photosensitive layer formed thereon will be low, and the printing durability of the printing plate will be extremely poor. On the other hand, if the surface roughness of the support is larger than 1.2 μm, the prints formed will often be stained. Color density of the support preferably falls between 0.15 and 0.65 in terms of reflection density. If this is smaller than 0.15, that is, if the support is too white, halation thereon in image exposure will be too strong and good images cannot be formed. On the other hand, if the color density of the support is larger than 0.65, that is, if the support is too dark, the images formed will be difficult to see in a process of image inspection after development, and image inspection efficiency will be greatly lowered.

As described above, the image-recording material of the present invention can be used in producing a planographic printing plate. An image can be recorded on the printing plate by exposing the photosensitive layer of the plate to IR radiation from an IR laser. As the case may be, image recording thereon may also be effected by exposing the photosensitive layer to a UV lamp or by thermally processing the layer with a thermal head. In the present invention, it is preferable that the photosensitive layer is imagewise exposed to IR radiation within a wavelength range of from 760 nm to 1200 nm from a solid laser or a semiconductor laser. Preferably, the laser output is at least 100 mW, and a multi-beam laser device is used for shortening time for exposure. Also preferably, the exposure time per one pixel is not longer than 20 μsec. Further preferably, the exposure energy to the recording material is between 10 and 300 mJ/cm$^2$.

After having been thus exposed to IR radiation from an IR laser, the image-recording material of the present invention is preferably developed with water or an aqueous alkali solution.

Immediately after having been illuminated with the laser radiation, the photosensitive layer of the material may be directly developed, but is preferably heated between the laser exposure step and the development step. Regarding the heating condition, the exposed layer is preferably heated at a temperature from 80° C. to 150° C. for a period of time from 10 seconds to 5 minutes. The heat treatment, if effected, may reduce the laser energy required for image exposure of the photosensitive layer.

The developer for the recording material of the invention is preferably an aqueous alkaline solution. More preferably, the aqueous alkaline solution serving as the developer has a pH falling between 10.5 and 12.5, even more preferably between 11.0 and 12.5. If the pH of the aqueous alkaline solution used for the developer is smaller than 10.5, the non-image area of the developed layer will be stained; but if larger than 12.5, the mechanical strength of the image area of the developed layer will lower.

In cases where the image-recording material of the present invention is, after exposure, developed with this aqueous alkaline solution, the developer and a replenisher for development may be any known aqueous alkaline solution. Usable, for example, are inorganic alkali salts such as sodium and potassium silicates, sodium, potassium and ammonium tertiary phosphates, sodium, potassium and ammonium secondary phosphates, sodium, potassium and ammonium carbonates, sodium, potassium and ammonium hydrogencarbonates, sodium, potassium and ammonium borates, and sodium, ammonium, potassium and lithium hydroxides. Also usable are organic alkalis such as monomethylamine, dimethylamine, trimethylamine, monoethylamine, diethylamine, triethylamine, monoisopropylamine, diisopropylamine, triisopropylamine, n-butylamine, monoethanolamine, diethanolamine, triethanolamine, monoisopropanolamine, diisopropanolamine, ethyleneimine, ethylenediamine, and pyridine.

One or more of these alkalis may be used singly or combined.

If an automatic processor is used, it is known that the replenisher, which is the same as the developer originally in the development tank or is an aqueous solution having a higher alkali concentration than the original developer, can replenish the development tank. In the processor of this system, a large number of planographic printing plates can be continuously processed even if the developer in the development tank is not exchanged for a long period of time. This replenishing system is favorable with the present invention.

If desired, various surfactants and organic solvents may be added to the developer and the replenisher, for promoting or retarding the development, for dispersing developer wastes, and for enhancing the affinity of the image area of the developed printing plate to ink.

Preferably, the developer contains from 1 to 20% by weight, more preferably from 3 to 10% by weight of a surfactant. If the surfactant content of the developer is smaller than 1% by weight, the developability with the developer could not be satisfactorily enhanced; but if larger than 20% by weight, it is unfavorable since the abrasion resistance and the mechanical strength of the image area of the developed layer will lower.

For the surfactant, preferred are anionic, cationic, nonionic or ampholytic surfactants. Concretely, they include sodiumlauryl alcohol sulfate, ammoniumlauryl alcohol sulfate, sodium octyl alcohol sulfate; alkylarylsulfonates such as sodium isopropylnaphthalenesulfonate, sodium isobutylnaphthalenesulfonate, sodium polyoxyethylene glycol mononaphthylether sulfate, sodium dodecylbenzenesulfonate, sodium metanitrobenzenesulfonate; higher alcohol sulfates having from 8 to 22 carbon atoms, such as secondary sodium alkylsulfates; salts of aliphatic alcohol phosphates such as sodium cetyl alcohol phosphate; alkylamide sulfonates such as $C_{17}H_{33}CON(CH_3)CH_2CH_2SO_3Na$; dibasic aliphatic ester sulfonates such as dioctyl sodiumsulfosuccinate, dihexyl sodiumsulfosuccinate; ammonium salts such as lauryltrimethylammonium chloride, lauryltrimethylammonium mesosulfate; amine salts such as stearamidoethyldiethylamine acetate; polyalcohol esters such as monoesters of fatty acids with glycerol, and monoesters of fatty acids with pentaerythritol; and polyethylene glycol ethers such as polyethylene glycol mononaphthyl ether, polyethylene glycol mono (nonylphenol) ether.

Preferably, the organic solvent that may be in the developer or replenisher has a solubility in water of at most about 10% by weight, more preferably at most 5% by weight. For example, it includes 1-phenylethanol, 2-phenylethanol, 3-phenylpropanol, 1,4-phenylbutanol, 2,2-phenylbutanol, 12-phenoxyethanol, 2-benzyloxyethanol, 0-methoxybenzyl alcohol, m-methoxybenzyl alcohol, p-methoxybenzyl alcohol, benzyl alcohol, cyclohexanol, 2-methylcyclohexanol, 4-methylcyclohexanol, and 3-methylcyclohexanol. Preferably, the organic solvent in the developer accounts for from 1 to 5% by weight of the developer in actual use. The organic solvent content of the developer is closely correlated to the surfactant content thereof. Preferably, with the increase in the organic solvent content of the developer, the surfactant content thereof increases. This is because, if the amount of the organic solvent in the developer increases when that of the surfactant therein is small, the organic solvent could not well dissolve in the developer; and if so, the developer could not exhibit good developability.

Also if desired, other additives such as defoaming agent and water softener may be added to the developer and the replenisher. The water softener includes, for example, polyphosphates such as $Na_2P_2O_7$, $Na_5P_3O_3$, $Na_3P_3O_9$, $Na_2O_4P(NaO_3P)PO_3Na_2$, Calgon (sodium polymetaphosphate); aminopolycarboxylic acids and their salts, such as ethylenediamine-tetraacetic acid and its potassium and sodium salts, diethylenetriamine-pentaacetic acid and its potassium and sodium salts, triethylenetetramine-hexaacetic acid and its potassium and sodium salts, hydroxyethylethylenediamine-triacetic acid and its potassium and sodium salts, nitrilotriacetic acid and its potassium and sodium salts, 1,2-diaminocyclohexane-tetraacetic acid and its potassium and sodium salts, and 1,3-diamino-2-propanol-tetraacetic acid and its potassium and sodium salts; and organic phosphonic acids and their salts, such as 2-phosphonobutane-tricarboxylic acid-1,2,4 and its potassium and sodium salts, 2-phosphonobutane-tricarboxylic acid-2,3,4 and its potassium and sodium salts, 1-phosphonoethane-tricarboxylic acid-1,2,2 and its potassium and sodium salts, 1-hydroxyethane-1,1-diphosphonic acid and its potassium and sodium salts, aminotri (methylenephosphonic acid) and its potassium and sodium salts. The optimum amount of the water softener to be in the developer varies, depending on the hardness of the hard water used and on the amount thereof to be in the developer. In general, the amount of the water softener to be in the developer in actual use may fall between 0.01 and 5% by weight, preferably between 0.01 and 0.5% by weight.

In case where the planographic printing plate are processed in such an automatic processor, the developer used is fatigued, depending on the amount of the plate processed. In such a case, a replenisher or a fresh developer may be replenished to the processor to thereby reactivate the developer in the processor. For this, preferably employed is the system described in U.S. Pat. No. 4,882,246.

Developers containing a surfactant, an organic solvent and a reducing agent such as those mentioned above are known. For example, JP-A No. 51-77401 discloses a developer comprising benzyl alcohol, an anionic surfactant, an alkali agent and water; JP-A No. 53-44202 discloses an aqueous developer containing benzyl alcohol, an anionic surfactant and a water-soluble sulfite; and JP-A No. 55-155355 discloses a developer containing an organic solvent, of which the solubility in water at room temperature is at most 10% by weight, an alkali agent and water. These are all favorable to the present invention.

After having been processed with a developer and a replenisher such as those mentioned above, the printing plates are post-processed with washing water, a rinsing solution that contains a surfactant, or a fat-desensitizing solution that contains gum arabic or a starch derivative. In cases where the image-recording material of the present invention is used in producing such printing plates, these post-treatments can be combined in any desired manner.

In recent art of processing printing plates and producing prints, automatic processors for printing plates are widely used for rationalizing and standardizing plate-processing operations. In general, the automatic processor is composed of a developing section and a post-processing section, and includes a unit for conveying printing plates to be processed, and processing solution tanks each equipped with a spraying unit. In these tanks: each exposed plate is conveyed horizontally and sprayed in succession with processing solutions that are pumped through spray nozzles, and is thus developed and processed. Besides this, each exposed plate can be guided in order into tanks filled with respective processing solutions, and guided therein by guide rolls, and thus developed and processed. In such automatic processors, replenishers may be replenished to the respective processing solutions, depending on the processing speed and the processing time. As the case may be, the replenishment may be automated by monitoring the electroconductivity of each processing solution with a sensor.

A processing system with no replenishment thereto is also employable, in which is used a disposable processing solution. In this, printing plates are processed with substantially unused processing solutions, with no replenisher being used.

The planographic printing plates produced in the above manner are optionally coated with a desensitizing gum, and then used in producing prints. For further enhancing printing durability, they may optionally be baked.

Prior to being baked, it is desirable that the planographic printing plates are treated with a baking conditioner, for example, as in JP-B Nos. 61-2518 and 55-28062, and JP-A Nos. 62-31859 and 61-159655.

For this, for example, the planographic printing plates may be wiped with a sponge or absorbent cotton that contains a baking conditioner; or they may be dipped in a baking conditioner in a vat; or a baking conditioner may be applied with an automatic coater. After having been thus coated with the baking conditioner, the plates are preferably squeezed with a squeegee or a squeezing roller so that the plates can be uniformly coated. This treatment produces better results.

The amount of the baking conditioner to be applied to the plates generally falls between 0.03 and 0.8 g/m$^2$ in terms of the dry weight of the baking conditioner.

The planographic printing plates having been thus coated with the baking conditioner are, after being optionally dried, heated at a high temperature in a baking processor (for example, BP-1300, a baking processor marketed by Fuji Photo Film Co., Ltd.). The heating temperature and heating time in this treatment vary, depending on the image-recording components in the plates. In general, it is desirable that the plates are heated at a temperature between 180 and 300° C., for 1 to 20 minutes.

After having been thus baked, the planographic printing plates may be washed with water, gummed and the like in a conventional manner as necessary. In cases where the plates are treated with a baking conditioner that contains a water-soluble polymer compound before being baked, a desensitization treatment, for example, the treatment of gumming, may be omitted.

The planographic printing plate thus produced by this process as above is set in an offset printer and used for producing a large number of prints.

EXAMPLES

The invention is described in detail with reference to the following Examples, which, however, are not intended to restrict the scope of the invention.

Synthesis Example
Synthesis of Cyanine Dye, IR-2

35.0 g of 5-chloro-1-ethyl-2,3,3-trimethyl-3H-indolium iodide and 26.5 g of N-(2,5-bis ((phenylamino)methylene) cyclopentylidene)-N-phenylbenzene-aminium tetrafluoroborate were dissolved in 380 ml of isopropyl alcohol, to which were added 10.2 g of acetic anhydride and 25.3 g of triethylamine, and heated under reflux for 2 hours. After this was left cooled, 20.9 g of aqueous 42% tetrafluoroboric acid solution and 15.0 g of acetic acid were added thereto and stirred at room temperature for 2 hours. The precipitate was taken out through filtration, washed with about 50 ml of ethyl acetate and then with 200 ml of water, and thereafter dried under reduced pressure to obtain 25.6 g of IR-2A corresponding to IR-2 but having $BF_4^-$ as the counter anion. The thus-obtained IR-2A was dissolved in 250 ml of N,N-dimethylformamide, and the resulting solution was poured into a solution of 58 g of sodium trifluoromethanesulfonate in 1500 ml of water. The precipitate was taken out through filtration, and dried. This operation was repeated twice again, and 25.4 g of IR-2 was thus obtained. The absorption peak wavelength in methanol of IR-2 is 794 nm; and the molar extinction coefficient thereof is $2.6 \times 10^5$. The structure of IR-2 was identified through $^1$H-NMR; and the conversion of the counter anion, from $BF_4^-$ to $CF_3SO_3^-$ was confirmed through $^{19}$F-NMR. The other cyanine dyes may be produced in the same manner as above.

Figure 2:
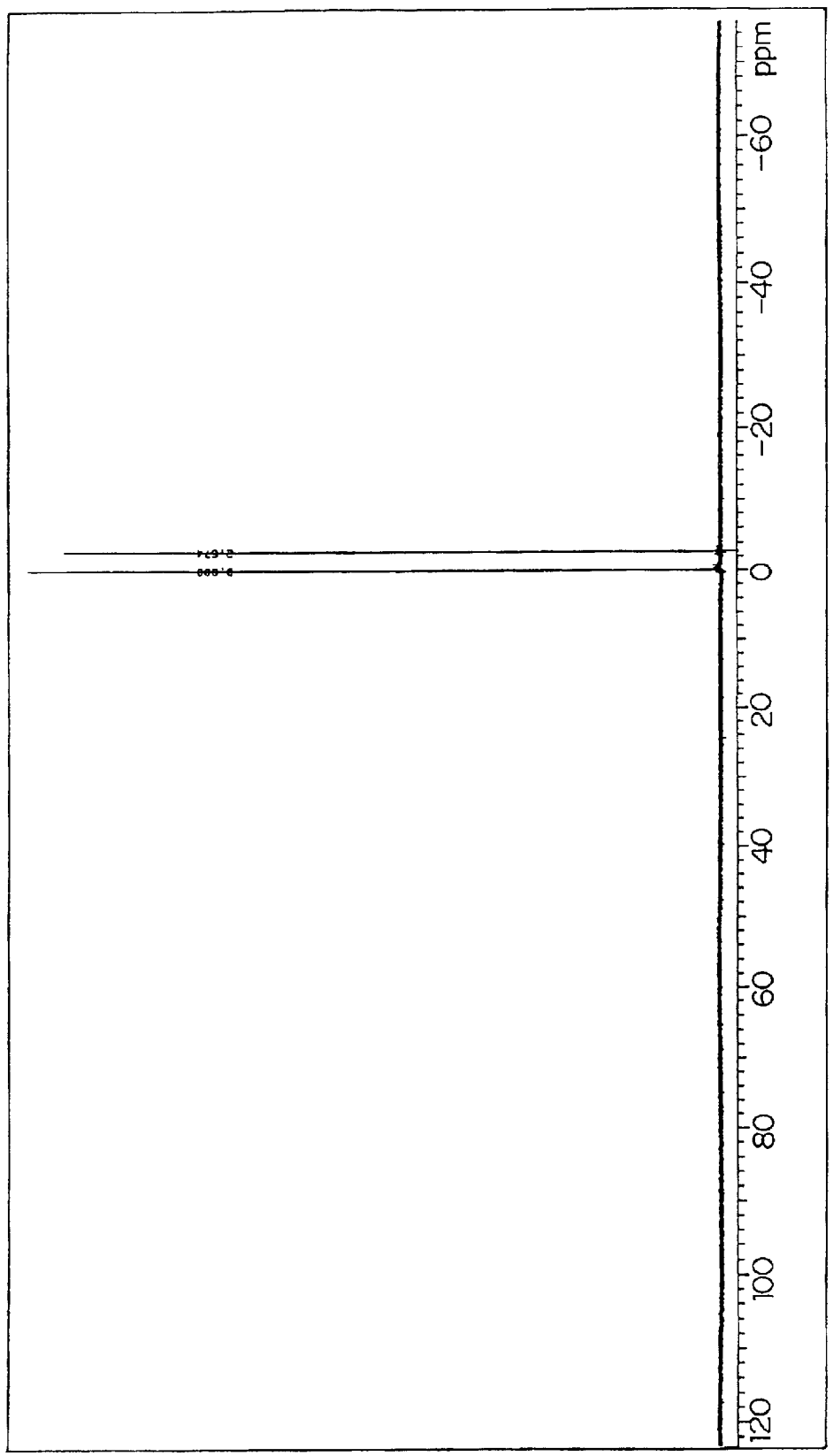
FIG. 2 is the $^{19}$F-NMR spectrum (DMSO-$d_6$) of IR-2.

FIG. 1 is the $^1$H-NMR spectrum (DMSO-d$_6$) of the IR absorbent, IR-2; and FIG. 2 is the $^{19}$F-NMR spectrum (DMSO-d$_6$) of IR-2. In FIG. 2, the signal seen at 0 ppm is from the reference, trifluoroacetic acid, and no signal from $BF_4^-$ is seen.

Examples 1 to 8
Preparation of Support

A melt of JIS A1050 alloy of at least 99.5% Al, containing 0.30% Fe, 0.10% Si, 0.02% Ti and 0.013% Cu was purified and cast. For purifying it, the alloy melt was degassed to remove the unnecessary gas such as hydrogen from it, and filtered through a ceramic tube filter. The alloy melt was cast in a mode of DC casting. The solidified ingot having a thickness of 500 mm was cut to a depth of 10 mm from its surface, and then homogenized at 550° C. for 10 hours with preventing the intermetallic compound therein from growing into coarse grains. Next, this was hot-rolled at 400° C., then annealed in a continuous annealing furnace at 500° C. for 60 seconds (this is process annealing), and thereafter cold-rolled into an aluminium sheet having a thickness of 0.30 mm. In this, the surface roughness of the roll used was so controlled that the center line average height, Ra, of the cold-rolled aluminium sheet could be 0.2 μm. The aluminium sheet was leveled with a tension leveler to thereby further increase its surface smoothness.

Next, the aluminium sheet was subjected to surface treatment in the manner mentioned below, so that it could be a support of a planographic printing plate.

Concretely, for removing the rolling oil from its surface, the aluminium sheet was degreased with aqueous 10% sodium aluminate solution at 50° C. for 30 seconds, then neutralized with aqueous 30% sulfuric acid at 50° C. for 30 seconds, and then desmutted.

Next, the surface of the aluminium sheet was electrolytically dressed and roughened. This is for improving the adhesiveness between the aluminium sheet serving as a support and a photosensitive layer to be formed thereon, and for ensuring water retentiveness in the non-image area of the printing plate having the aluminium sheet support. Concretely, an aqueous solution containing 1% nitric acid and 0.5% aluminium nitrate was prepared and kept at 45° C., and a web of the aluminium sheet was passed through it with applying an alternating electric current (duty ratio: 1/1) to the web from an indirect electric cell. The current density was 20 A/cm², and the quantity of electricity at the anode was 240 C/dm². After having been thus electrolytically dressed, the aluminium sheet web was etched in aqueous 10% sodium aluminate solution at 50° C. for 30 seconds, then neutralized in aqueous 30% sulfuric acid solution at 50° C. for 30 seconds, and thereafter desmutted.

For improving its abrasion resistance, chemical resistance and water retentiveness, the aluminium sheet web was subjected to anodic oxidation to form an oxide film thereon. Concretely, the aluminium sheet web was passed through an aqueous electrolytic solution of 20% sulfuric acid at 35° C. and electrolyzed therein with a direct current of 14 A/dm² being applied thereto from an indirect electric cell. Through the anodic oxidation, the aluminium sheet web had an oxide film of 2.5 g/m² formed thereon.

Next, this was treated with a silicate. This treatment is for ensuring the hydrophilicity of the non-image area of the printing plate having the aluminium sheet support. Concretely, the aluminium sheet web was passed through aqueous 1.5% #3 sodium silicate solution at 70° C. The contact time was 15 seconds. Then, this was washed with water. The amount of Si deposited on the web was 10 mg/m². The center line average height, Ra, of the thus-processed aluminium sheet was 0.25 μm. The aluminium sheet serves as the support of the printing plate produced herein.

Undercoating

Next, the aluminium support was coated with an undercoating liquid (its composition is shown below) by the use of a wire bar, and dried in a hot air drier at 90° C. for 30 seconds. After dried, the thickness of the undercoat layer formed was 10 mg/m².

Undercoating Liquid

| | |
|---|---|
| Copolymer of ethyl methacrylate and sodium 2-acrylamido-2-methyl-1-propanesulfonate, 75/15 by mol | 0.1 g |
| 2-Aminoethylphosphonic acid | 0.1 g |
| Methanol | 50 g |
| Ion-exchange water | 50 g |

Photosensitive Layer:

Next, a coating liquid for photosensitive layer [P] (its composition is shown below) was prepared. Immediately after its preparation, the liquid [P] was applied to the undercoated aluminium sheet by the use of a wire bar, and then dried in a hot air drier at 115° C. for 45 seconds. In that manner, negative planographic printing plates precursors [P-1] to [P-8] were produced. After dried, the amount of the photosensitive layer formed on each precursor was 1.3 g/m². The IR absorbent and the radical generator used in the coating liquid [P] are shown in Table 9. The reflection density at the absorption peak in the IR range of the photosensitive layer of each precursor was measured. Of all precursors, the reflection density fell between 0.6 and 1.2.

Coating Liquid [P] for Photosensitive Layer:

| | |
|---|---|
| IR absorbent (shown in Table 9) | 0.10 g |
| Radical generator (shown in Table 9) | 0.30 g |
| Dipentaerythritol hexaacrylate | 1.00 g |
| Copolymer of allyl methacrylate and methacrylic acid, 80/20 by mol (weight-average molecular weight: 120,000) | 1.00 g |
| Victoria Pure Blue naphthalenesulfonate | 0.04 g |
| Fluorine-containing surfactant (Dai-Nippon Ink Chemical Industry's Megafac F-176) | 0.01 g |
| Methyl ethyl ketone | 9.0 g |
| Methanol | 10.0 g |
| 1-Methoxy-2-propanol | 8.0 g |

TABLE 9

| | Planographic Printing Plate Precursor | IR Absorbent | Radical Generator |
|---|---|---|---|
| Example 1 | [P-1] | IR-2 | OI-5 |
| Example 2 | [P-2] | IR-2 | ON-2 |
| Example 3 | [P-3] | IR-2 | OS-4 |
| Example 4 | [P-4] | IR-5 | OS-4 |
| Example 5 | [P-5] | IR-2 | OS-6 |
| Example 6 | [P-6] | IR-12 | OS-6 |
| Example 7 | [P-7] | IR-2 | Initiator A |
| Example 8 | [P-8] | IR-2 | Initiator B |
| Comp. Ex. 1 | [Q-1] | IR-786 | OI-5 |
| Comp. Ex. 2 | [Q-2] | perchlorate | ON-2 |
| Comp. Ex. 3 | [Q-3] | | OS-4 |

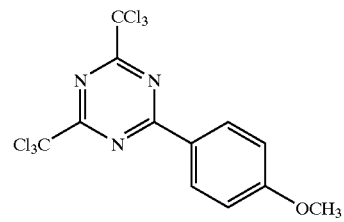

Initiator A

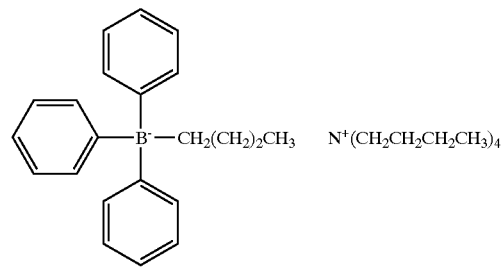

Initiator B

Exposure:

The negative planographic printing plate precursors [P-1] to [P-8] were imagewise exposed to IR rays, using Creo's Trendsetter 3244VFS with a water-cooling 40 W IR semi-conductor laser mounted thereon. The laser power was 9 W; the drum revolution was 210 rpm; the energy on the plate was 100 mJ/cm²; and the image resolution was 2400 dpi.

Development:

After having been thus exposed, the plates were processed by the use of an automatic processor, Fuji Photo Film's Stablon 900 N. For both the original developer and the replenisher, used was Fuji Photo Film's DN-3C, diluted with water to 1/1. The temperature of the developer bath was 30° C. For the finisher, used was Fuji Photo Film's FN-6, diluted with water to 1/1 (pH=10.8).

Evaluation of Printability of Printing Plates:

The thus-processed planographic printing plates [P-1] to [P-8] were tested for their printability. Concretely, each printing plate was set in a Heidelberg's printer, Heidel SOR-M, which was driven to give prints with commercially-available oily ink. The prints were macroscopically checked for stains in their non-image area. The results are given in Table 10. No stains were found in all prints from all the printing plates tested.

Number of Good Prints:

Next, the planographic printing plates [P-1] to [P-8] were tested in a Komori Corporation's printer, Lithlon, to check how many good prints could be obtained from them. Concretely, all the prints were macroscopically checked for their ink density, and the number of good prints from each printing plate tested was counted. The results are given in Table 10.

Comparative Examples 1 to 3

A coating liquid for photosensitive layer [P] was prepared in the same manner as in Examples 1 to 3, in which, however, a Sigma Aldrich Japan's IR absorbent, IR-786 perchlorate (its oxidation potential is 0.53 V vs. SCE) was used in place of the IR absorbent of the invention. The chemical structure of IR-786 perchlorate is shown below. The coating liquid thus prepared was applied to a support of the undercoated aluminium sheet, and dried. The comparative, planographic printing plate precursors thus produced herein are referred to as [Q-1] to [Q-3]. The details of the radical generator used herein are shown in Table 9.

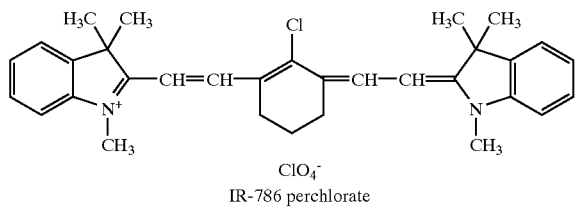

IR-786 perchlorate

These planographic printing plate precursors [Q-1] to [Q-3] were exposed and processed in the same manner as in Examples 1 to 8 in to planographic printing plates [Q-1] to [Q-3]. Also in the same manner as in Examples 1 to 8, these printing plates were tested for their printability. The prints from them were macroscopically checked f or stains in their non-image area. The results are given in Table 10.

TABLE 10

| | Planographic Printing Plate | Stains in Non-image Area | Number of Good Prints |
|---|---|---|---|
| Example 1 | [P-1] | no | 65,000 |
| Example 2 | [P-2] | no | 60,000 |
| Example 3 | [P-3] | no | 60,000 |
| Example 4 | [P-4] | no | 75,000 |
| Example 5 | [P-5] | no | 70,000 |
| Example 6 | [P-6] | no | 65,000 |
| Example 7 | [P-7] | no | 55,000 |
| Example 8 | [P-8] | no | 60,000 |
| Comp. Ex. 1 | [Q-1] | no | 45,000 |
| Comp. Ex. 2 | [Q-2] | yes, a little | 40,000 |
| Comp. Ex. 3 | [Q-3] | no | 30,000 |

As is obvious from Table 10, the planographic printing plates of the invention, in which the photosensitive layer contained an IR absorbent having an electron-withdrawing substituent or a heavy atom-containing substituent, gave a larger number of good prints with no stain in their non-image area, even though they were imagewise exposed and then developed and processed with out being heated after the exposure. However, the number of good prints from the comparative printing plates, in which the IR absorbent in the photosensitive layer is outside the scope of the invention, is smaller than that from the printing plates of the invention.

Examples 9 and 10

A coating liquid for photosensitive layer [R] (its composition is shown below) was prepared. Immediately after its preparation, the coating liquid [R] was applied to the undercoated aluminium sheet (this was prepared in the same manner as in Examples 1 to 8) by the use of a wire bar, and then dried in a hot air drier at 115° C. for 45 seconds. In that manner, negative planographic printing plate precursors [R-1] and [R-2] were produced. After dried, the amount of the photosensitive layer formed on each precursor was 1.3 g/m². The IR absorbent and the radical generator used in the coating liquid [R] are shown in Table 11.

Coating Liquid for Photosensitive Layer [R]:

| | |
|---|---|
| IR absorbent (shown in Table 11) | 0.10 g |
| Radical generator (shown in Table 11) | 0.30 g |
| Polyfunctional monomer (its structure is shown below) | 1.00 g |
| Addition copolymer of 4,4'-diphenylmethane diisocyanate, hexamethylene diisocyanate, tetraethylene glycol, and 2,2-bis (hydroxymethyl) propionic acid, 30/20/30/20 by mol (weight-average molecular weight: 60,000) | 1.00 g |
| Victoria Pure Blue naphthalenesulfonate | 0.04 g |
| Fluorine-containing surfactant (Dai-Nippon Ink Chemical Industry's Megafac F-176) | 0.01 g |
| Methyl ethyl ketone | 5.0 g |
| Methanol | 10.0 g |
| 1-Methoxy-2-propanol | 8.0 g |
| Methyl lactate | 2.0 g |
| γ-butyrolactone | 2.0 g |

Structural Formula of Monomer:

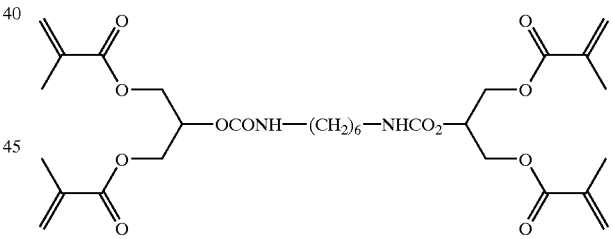

TABLE 11

| | Planographic Printing Plate Precursor | IR Absorbent | Radical Generator |
|---|---|---|---|
| Example 9 | [R-1] | IR-1 | OS-4 |
| Example 10 | [R-2] | IR-22 | OS-6 |
| Comp. Ex. 4 | [S-1] | IR-768 perchlorate | OS-4 |

Exposure:

The negative planographic printing plate precursors [R-1] and [R-2] were imagewise exposed to light, using Fuji Photo Film's Luxel T-9000CTP with a multi-channel laser head mounted thereon. The power was 250 mW/beam; the drum revolution was 800 rpm; and the image resolution was 2400 dpi.

After thus exposed, these were processed in the same manner as in Examples 1 to 8 into planographic printing plates [R-1] and [R-2]. Also in the same manner as in Examples 1 to 6, these printing plates [R-1] and [R-2] were tested for their printability, and the number of good prints from them was counted. The results are given in Table 12 below.

Comparative Example 4

A coating liquid for photosensitive layer [R] was prepared in the same manner as in Examples 9 and 10, in which, however, a Sigma Aldrich Japan's IR absorbent, IR-768 perchlorate (its oxidation potential is 0.49 V vs. SCE, and its structure is shown below) was used in place of the IR absorbent of the invention. Immediately after its preparation, the coating liquid was applied to the same aluminium support as in Examples 1 to 8, and dried. The comparative, planographic printing plate precursor thus produced herein is referred to as [S-1]. The details of the radical generator used herein are shown in Table 11 given above.

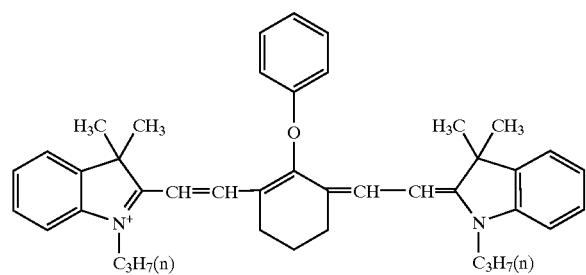

The planographic printing plate precursor [S-1] was exposed and processed in the same manner as in Examples 9 and 10 into a planographic printing plate [S-1]. Also in the same manner as in Examples 9 and 10, the printing plate was tested for its printability. The prints from it were macroscopically checked for stains in their non-image area. The results are given in Table 12.

TABLE 12

|  | Planographic Printing Plate | Stains in Non-image Area | Number of Good Prints |
|---|---|---|---|
| Example 9 | [R-1] | no | 50,000 |
| Example 10 | [R-2] | no | 55,000 |
| Comp. Ex. 4 | [S-1] | no | 20,000 |

As is obvious from Table 12, the planographic printing plates of the invention, [R-1] and [R-2] gave a larger number of good prints with no stain in their non-image area.

However, the number of good prints from the comparative printing plate, [S-1] which differs from the printing plate of Example 9 of the invention only in that the IR absorbent in the photosensitive layer in the former is outside the scope of the invention, is smaller than that from the printing plates of the invention.

Examples 11 to 14, Comparative Examples 5 and 6

Preparation of Support:

An aluminium support was prepared in the same manner as in Examples 1 to 8, except that it was not subjected to the silicate treatment for hydrophilication.

Undercoating:

Next, the aluminium support was coated with a coating liquid for undercoat layer (its composition is shown below) by the use of a wire bar, and dried in a hot air drier at 90° C. for 30 seconds. After dried, the thickness of the undercoat layer formed was 10 Mg/m$^2$.

Coating Liquid for Undercoat Layer

| β-alanine | 0.1 g |
|---|---|
| Phenylphosphonic acid | 0.1 g |
| Methanol | 40 g |
| Pure water | 60 g |

Photosensitive Layer:

A coating liquid for photosensitive layer [P] was prepared in the same manner as in Examples 1 to 6, in which, however, an IR absorbent and a radical generator both shown in Table 13 below were used. Also in the same manner as in Examples 1 to 6, the coating liquid thus prepared was applied to the undercoated aluminium sheet by the use of a wire bar, and then dried. In that manner, negative planographic printing plate precursors [P-9] to [P-12] and [Q-5] and [Q-6] were produced.

TABLE 13

|  | Planographic Printing Plate Precursor | IR Absorbent | Radical Generator |
|---|---|---|---|
| Example 11 | [P-9] | IR-22 | OI-5 |
| Example 12 | [P-10] | IR-2 | OS-4 |
| Example 13 | [P-11] | IR-22 | OS-6 |
| Example 14 | [P-12] | IR-5 | OS-6 |
| Comp. Ex. 5 | [Q-5] | IR-786 | OI-5 |
| Comp. Ex. 6 | [Q-6] | perchlorate | OS-6 |

These planographic printing plate precursors, [P-9] to [P-12] and [Q-5] and [Q-6] were exposed and processed in the same manner as in Examples 1 to 8, except that the developer mentioned below was used for these. Thus processed, the planographic printing plates are referred to as [P-9] to [P-12] and [Q-5] and [Q-6].

Developer:

| Potassium hydroxide | 3.8 g |
|---|---|
| Polyethylene glycol mononaphthyl ether | 250 g |
| Sodium ethylenediaminetetraacetate | 8 g |
| Water | 738 g |
| (pH = 11.7) | |

Also in the same manner as in Examples 1 to 8, these printing plates were tested for their printability. The prints from them were macroscopically checked for stains in their non-image area. The results are given in Table 14.

TABLE 14

|  | Planographic Printing Plate | Stains in Non-image Area | Number of Good Prints |
|---|---|---|---|
| Example 11 | [P-9] | no | 65,000 |
| Example 12 | [P-10] | no | 75,000 |
| Example 13 | [P-11] | no | 65,000 |
| Example 14 | [P-12] | no | 75,000 |
| Comp. Ex. 5 | [Q-5] | no | 45,000 |
| Comp. Ex. 6 | [Q-6] | no | 40,000 |

As is obvious from Table 14, the planographic printing plates of the invention, [P-9] to [P-12] gave a larger number of good prints with no stain in their non-image area.

However, the number of good prints from the printing plates of Comparative Examples 5 and 6, which differ from the printing plates of Examples 11 and 13 of the invention only in that the IR absorbent in the photosensitive layer in the former is outside the scope of the invention, is smaller than that from the printing plates of the invention.

Examples 15 to 20, Comparative Examples 7 to 9

An aluminium support was prepared in the same manner as in Examples 1 to 6, except that it was not subjected to the silicate treatment. This was coated with a coating liquid for undercoat layer (its composition is shown below), and dried at 80° C. for 30 minutes. The dry weight of the undercoat layer was 10 mg/m$^2$.

Coating Liquid for Undercoat Layer:

The following compounds were mixed to prepare a coating liquid for undercoat layer.

| | |
|---|---|
| 2-Aminoethylphosphonic acid | 0.5 g |
| Methanol | 40 g |
| Pure water | 60 g |

Formation of Resin Interlayer:

A coating liquid for resin interlayer [A] mentioned below was applied onto the undercoated support by the use of a wire bar, and dried in a hot air drier at 120° C. for 45 seconds to form a resin interlayer thereon. The dry weight of the resin interlayer was 0.5 mg/m$^2$.

Coating Liquid for Resin Interlayer [A]:

| | |
|---|---|
| Polymer compound (copolymer of N-(p-aminosulfonylphenyl)methacrylamide and butyl acrylate, 35/65 by mol, having a weight-average molecular weight of 60,000) | 0.5 g |
| Victoria Pure Blue naphthalenesulfonate | 0.01 g |
| Fluorine-containing surfactant (Dai-Nippon Ink Chemical Industry's Megafac F-176) | 0.01 g |
| Methyl ethyl ketone | 10 g |
| γ-butyrolactone | 7 g |
| Dimethylsulfoxide | 5 g |
| Methanol | 5 g |

Formation of Photosensitive Layer:

The same coating liquid for photosensitive layer as in Examples 1 to 6 and Comparative Examples 1 to 3 was prepared, except that the solvent, 1-methoxy-2-propanol was substituted with ethyl acetate. In the two, the amount of the solvent was the same. Using a wire bar, the coating liquid prepared herein was applied onto the resin interlayer formed on the support, and then dried in a hot air drier at 110° C. for 45 seconds to thereby form a photosensitive layer on the resin interlayer. The planographic printing plate precursors thus fabricated herein are referred to as [P-13] to [P-18] and [Q-7] to [Q-9]. The dry weight of the photosensitive layer was 1.2 mg/m$^2$.

The planographic printing plate precursors [P-13] to [P-18] and [Q-7] to [Q-9] of which the photosensitive layer was formed via the resin interlayer were exposed in the same manner as in Examples 1 to 6, and then processed in an automatic processor, Fuji Photo Film's Stablon 900NP having a developer [2] therein. The composition of the developer [2] is shown below. Also in the same manner as in Examples 1 to 6, the thus-processed printing plates were tested for their printability. The results are given in Table 15.

Developer [2]:

This is an aqueous solution containing 1.5 wt. % KOH, 1.0 wt. % SiO$_2$, and 2 wt. % sodium dibutylnaphthalenesulfonate.

TABLE 15

| | Planographic Printing Plate | Stains in Non-image Area | Number of Good Prints |
|---|---|---|---|
| Example 15 | [P-13] | no | 85,000 |
| Example 16 | [P-14] | no | 85,000 |
| Example 17 | [P-15] | no | 80,000 |
| Example 18 | [P-16] | no | 85,000 |
| Example 19 | [P-17] | no | 90,000 |
| Example 20 | [P-18] | no | 85,000 |
| Comp. Ex. 7 | [Q-7] | no | 50,000 |
| Comp. Ex. 8 | [Q-8] | no | 45,000 |
| Comp. Ex. 9 | [Q-9] | no | 40,000 |

As is obvious from Table 15, the planographic printing plates of the invention, in which the photosensitive layer contained an IR absorbent having an electron-withdrawing substituent or a heavy atom-containing substituent, gave a larger number of good prints with no stain in their non-image area, even though they were imagewise exposed and then developed and processed without being heated after the exposure. However, the number of good prints from the comparative printing plates, in which the IR absorbent in the photosensitive layer is outside the scope of the invention, is smaller than that from the printing plates of the invention.

Reference Example 1

The planographic printing plate precursor [P-10] of Example 12 was exposed and processed into a planographic printing plate in the same manner as in Example 12, except that a developer, Fuji Photo Film's HD-P2 (pH=13.3) was used herein. Compared with that of the planographic printing plate of Example 12 in which the pH of the developer used for processing the plate falls within the above-mentioned preferred range, the printing durability of the image area of the printing plate of this Reference Example 1 was low and the non-image area of the printing plate stained a little.

Reference Example 2

The planographic printing plate precursor [P-10] of Example 12 was exposed and processed into a planographic printing plate in the same manner as in Example 12, except that a Wako Pure Chemical Industry's standard buffer (pH=10.01) was used as the developer herein. Compared with that in the plate having been processed with the preferred developer in Example 12, the non-image area in the plate processed herein did not dissolve completely, and the prints from the printing plate of this Reference Example 2 stained a little.

Reference Example 3

The planographic printing plate precursor [P-3] of Example 3 was, after heated on a hot plate at 160° C. for 90 seconds, processed in the same manner as in Examples 1 to 8. As cured through the heat treatment, the photosensitive layer of the plate [P-3] did not dissolve through development, like the image area of the photosensitive layer of the plate of Example 3. This means that the image formation on the layer of the negative image-recording material of the invention is not limited to only exposure to IR lasers but may be effected through directly heating the layer with a thermal head or the like.

Reference Example 4

The planographic printing plate precursor [P-3] of Example 3 was exposed to a xenon lamp via a Toshiba Glass' glass filter, R-69 disposed between the plate precursor and the lamp. Measured with an Advantest's power meter at the determined wavelength of 830 nm, the quantity of light on the surface of the plate precursor was 100 mV. After having been thus exposed for 60 seconds (this corresponds to an exposure amount of 6000 mJ/cm$^2$) the plate was processed in the same manner as in Examples 1 to 8. However, the photosensitive layer dissolved completely, leaving no film corresponding to the image area. From this, it is understood that, through photon-mode exposure, substantially no image is formed on the layer of the negative image-recording material of the invention, and the recording material of the invention requires heat-mode exposure for image formation thereon.

While the invention has been described in detail and with reference to specific embodiments thereof, it will be apparent to one skilled in the art that various changes and modifications can be made therein without departing from the spirit and scope thereof.

What is claimed is:

1. A negative image-recording material for heat-mode exposure systems, which comprises (A) an IR absorbent including cyanine dye having an electron-withdrawing group or a heavy atom-containing substituent in at least one terminal aromatic ring, (B) a radical generator and (C) a radically-polymerizable compound, wherein images are formed therein by imagewise exposure to IR rays.

2. A negative image-recording material for heat-mode exposure systems, which comprises (A') an IR absorbent of the following general formula (1), (B) a radical generator and (C) a radically-polymerizable compound, wherein images are formed therein by imagewise exposure to IR rays:

$$A^+ - Q = B \ X^- \tag{1}$$

wherein

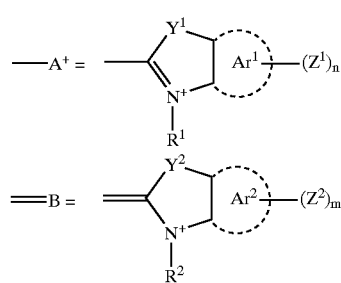

wherein A$^+$ and B are terminal groups represented by the formulae mentioned above;

R$^1$ and R$^2$ each independently represent an optionally-substituted hydrocarbon group having at most 20 carbon atoms; Ar$^1$ and Ar$^2$ may be the same or different, each representing an optionally-substituted aromatic hydrocarbon group or heterocyclic group;

Y$^1$ and Y$^2$ may be the same or different, each representing a sulfur atom, an oxygen atom, a selenium atom, a dialkylmethylene group having at most 12 carbon atoms, or —CH=CH—;

Z$^1$ and Z$^2$ may be the same or different, each representing a substituent selected from a hydrocarbon group, an oxy group, an electron-withdrawing substituent and a heavy atom-containing substituent, and at least one of these is an electron-withdrawing group or a heavy atom-containing substituent;

n and m each independently indicate 0 or a positive integer, and the sum of n and m is at least 1;

Q represents a pentamethine group or a heptamethine group, optionally substituted by substituent(s) selected from an alkoxy group, an aryloxy group, an alkylthio group, an arylthio group, a dialkylamino group, a diarylamino group, an halogen atom, an alkyl group, an aralkyl group, a cycloalkyl group, an aryl group, an oxy group, an iminium base, and a substituent of the following general formula (2), and Q may have a cyclohexene, cyclopentene or cyclobutene ring containing continuous three methine chains:

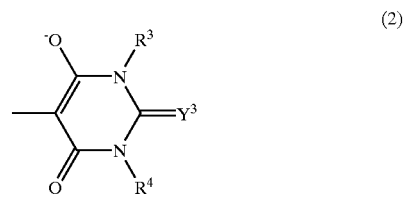

wherein R$^3$ and R$^4$ each independently represent a hydrogen atom, an alkyl group having from 1 to 8 carbon atoms, or an aryl group having from 6 to 10 carbon atoms;

Y$^3$ represents an oxygen atom or a sulfur atom;

X$^-$ represents a counter anion optionally existing for charge neutralization of the compound of formula (1).

3. A negative image-recording material for heat-mode exposure systems, which comprises (A") an IR absorbent of the following general formula (3), (B) a radical generator and (C) a radically-polymerizable compound, wherein images are formed therein by imagewise exposure to IR rays:

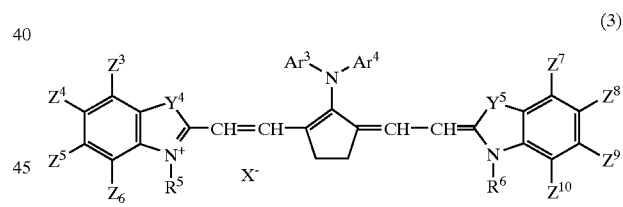

wherein R$^5$ and R$^6$ each independently represent a linear or branched alkyl group having at most 20 carbon atoms, optionally substituted with any of an aryl group, an alkenyl group, an alkoxy group, a hydroxyl group, a sulfo group, a carboxyl group and an acyloxy group;

Ar$^3$ and Ar$^4$ each independently represent a hydrogen atom, an alkyl group having from 1 to 4 carbon atoms, or an aryl group having from 6 to 10 carbon atoms, the alkyl group and the aryl group for these may be optionally substituted with any of an alkyl group, an aryl group and a halogen atom, and Ar$^3$ and Ar$^4$ may be bonded to each other;

Y$^4$ and Y$^5$ maybe the same or different, each representing a sulfur atom, an oxygen atom, a selenium atom, a dialkylmethylene group having at most 12 carbon atoms, or —CH=CH—;

Z$^3$ to Z$^{10}$ may be the same or different, each representing a hydrogen atom, a hydrocarbon group, an oxy group, an electron-withdrawing group or a heavy atom-containing substituent, and at least one of these is an electron-withdrawing group or a heavy atom-containing substituent, and two neighboring groups of $Z^3$ to $Z^{10}$ may be bonded to each other to form a 5- or 6-membered ring;

$X^-$ represents a counter anion optionally existing for charge neutralization of the compound of formula (1).

4. The negative image-recording material for heat-mode exposure systems as claimed in claim 2, wherein $X^-$ is selected form a halide, a perchlorate, a tetrafluoroborate, a hexafluorophosphate and a sulfonate.

5. The negative image-recording material for heat-mode exposure systems as claimed in claim 2, wherein $X^-$ is selected form a perchlorate and a sulfonate.

6. The negative image-recording material for heat-mode exposure systems as claimed in claim 3, wherein $X^-$ is selected form a halide, a perchlorate, a tetrafluoroborate, a hexafluorophosphate and a sulfonate.

7. The negative image-recording material for heat-mode exposure systems as claimed in claim 3, wherein $X^-$ is selected form a perchlorate and a sulfonate.

8. The negative image-recording material for heat-mode exposure systems as claimed in claim 1, wherein the electron-withdrawing group in the cyanine dye has a Hammett's substituent constant, $\sigma_{para}$, of at least 0.01.

9. The negative image-recording material for heat-mode exposure systems as claimed in claim 1, wherein the heavy atom in the heavy atom-containing substituent in the cyanine dye has an atomic weight of at least 28.

10. The negative image-recording material for heat-mode exposure systems as claimed in claim 9, wherein the heavy atom having an atomic weight of at least 28 is selected from silicon, phosphorus, sulfur, chlorine, germanium, arsenic, selenium, bromine, tin, antimony, tellurium and iodine.

11. The negative image-recording material for heat-mode exposure systems as claimed in claim 1, wherein the IR absorbent is selected from the following compounds:

IR-1
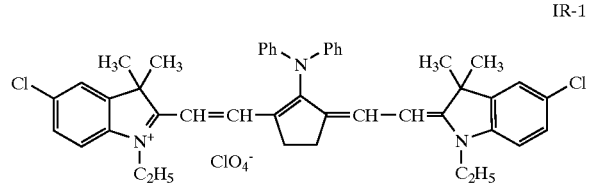

IR-2
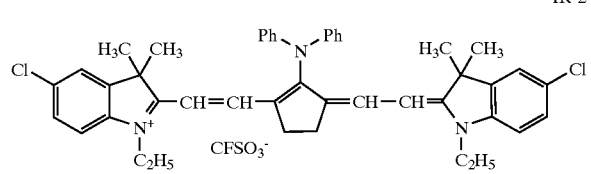

IR-5
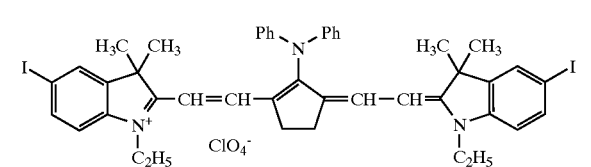

-continued

IR-12
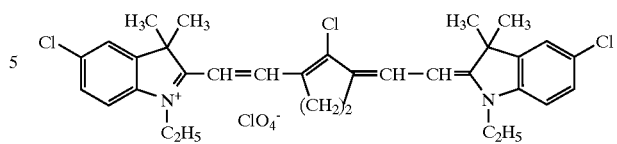

IR-22
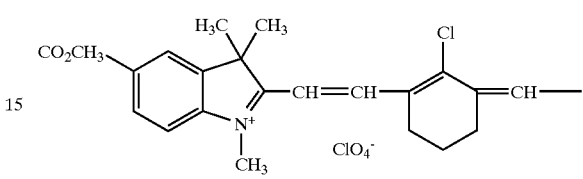

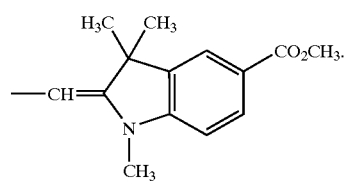

12. The negative image-recording material for heat-mode exposure systems as claimed in claim 2, wherein the IR absorbent is the following compound:

IR-2
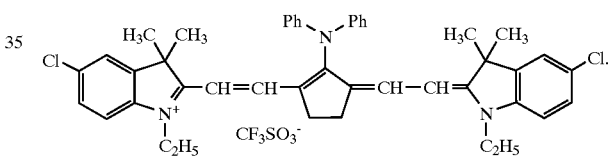

13. The negative image-recording material for heat-mode exposure systems as claimed in claim 1, wherein the radical generator is an onium salt.

14. The negative image-recording material for heat-mode exposure systems as claimed in claim 2, wherein the radical generator is an onium salt.

15. The negative image-recording material for heat-mode exposure systems as claimed in claim 13, wherein the onium salt is selected from a diazonium salt, an iodonium salt and a sulfonium salt.

16. The negative image-recording material for heat-mode exposure systems as claimed in claim 13, wherein the onium salt is a sulfonium salt.

17. The negative image-recording material for heat-mode exposure systems as claimed in claim 14, wherein the onium salt is selected from a diazonium salt, an iodonium salt and a sulfonium salt.

18. The negative image-recording material for heat-mode exposure systems as claimed in claim 14, wherein the onium salt is a sulfonium salt.

19. The negative image-recording material for heat-mode exposure systems as claimed in claim 1, which has a resin interlayer between a recording layer comprising the IR absorbent, the radical generator and the radically-polymerizable compound, and the support.

20. The negative image-recording material for heat-mode exposure systems as claimed in claim 2, which has a resin interlayer between a recording layer comprising the IR absorbent, the radical generator and the radically-polymerizable compound, and the support.

21. The negative image-recording material for heat-mode exposure systems as claimed in claim 1, which further contains a colorant.

22. The negative image-recording material for heat-mode exposure systems as claimed in claim 2, which further contains a colorant.

23. The negative image-recording material for heat-mode exposure systems as claimed in claim 19, which has a protective layer.

24. The negative image-recording material for heat-mode exposure systems as claimed in claim 20, which has a protective layer.

25. The negative image-recording material for heat-mode exposure systems as claimed in claim 1, which further comprises a binder polymer.

26. The negative image-recording material for heat-mode exposure systems as claimed in claim 25, wherein the binder polymer is an alkali-soluble resins having a double bond in the side chain.

27. The negative image-recording material for heat-mode exposure systems as claimed in claim 1, which further comprises a binder polymer.

28. The negative image-recording material for heat-mode exposure systems as claimed in claim 27, wherein the binder polymer is an alkali-soluble resins having a double bond in the side chain.

* * * * *